(12) United States Patent
Blatcher et al.

(10) Patent No.: US 10,357,194 B2
(45) Date of Patent: Jul. 23, 2019

(54) CATHETER

(75) Inventors: Stephen Blatcher, Cambridgeshire (GB); Richard Harley Greenville Owen, Cambridgeshire (GB); Joseph Peter Corrigan, Cambridgeshire (GB); Thomas Neudeck, Hoboken, NJ (US); Andrew Peter Scudamore, Cambridgeshire (GB); Yannick Pierre Louis Hourmand, Cambridgeshire (GB)

(73) Assignee: PLAQUETEC LTD., London (GB)

( * ) Notice: Subject to any disclaimer, the term of this patent is extended or adjusted under 35 U.S.C. 154(b) by 2495 days.

(21) Appl. No.: 12/355,486

(22) Filed: Jan. 16, 2009

(65) Prior Publication Data

US 2009/0187083 A1   Jul. 23, 2009

(30) Foreign Application Priority Data

Jan. 18, 2008   (GB) .................... 0800981.3

(51) Int. Cl.
*A61B 5/153*   (2006.01)
*A61B 5/00*   (2006.01)
(Continued)

(52) U.S. Cl.
CPC .......... *A61B 5/153* (2013.01); *A61B 5/15003* (2013.01); *A61B 5/150282* (2013.01); *A61B 5/150389* (2013.01); *A61B 5/150511* (2013.01); *A61B 5/150755* (2013.01); *A61B 5/417* (2013.01); *A61M 25/00* (2013.01)

(58) Field of Classification Search
CPC ..... A61M 25/00; A61B 10/0045; A61B 10/02

USPC .......... 600/581, 585, 573; 604/101.04, 268; 606/159; 607/106; 435/7.4
See application file for complete search history.

(56) References Cited

U.S. PATENT DOCUMENTS

| | | | |
|---|---|---|---|
| 3,384,170 A | 5/1968 | Van Poollen | |
| 3,516,410 A * | 6/1970 | Salomon | ............... A61M 1/008 604/268 |

(Continued)

FOREIGN PATENT DOCUMENTS

| | | |
|---|---|---|
| GB | 1405556 A | 9/1975 |
| GB | 2003388 A | 3/1979 |

(Continued)

OTHER PUBLICATIONS

Office Action dated Apr. 3, 2012 in JP 2008-512921 (JP2008545466A).
(JP Office Action in U.S. Appl. No. 13/105,726 dated Jun. 5, 2012).
(Continued)

*Primary Examiner* — Daniel L Cerioni

(57) ABSTRACT

A catheter and associated method for taking a plurality of samples from within a length of a blood vessel. The catheter includes an elongate central body arranged to be inserted into and positioned along a central region of a blood vessel. A plurality of collection areas are defined along the elongate central body for collecting samples at the central region of the blood vessel. A plurality of mixers are provided radially outwardly of the elongate central body and arranged to create a flow of blood from a boundary layer at a wall of the blood vessel to the elongate central body. This enables the collection areas to collect samples from the boundary layer.

32 Claims, 11 Drawing Sheets

(51) Int. Cl.
*A61M 25/00* (2006.01)
*A61B 5/15* (2006.01)

(56) References Cited

U.S. PATENT DOCUMENTS

| | | | |
|---|---|---|---|
| 3,595,241 A | | 7/1971 | Sheridan |
| 3,626,950 A | * | 12/1971 | Schulte .......................... 604/268 |
| 4,072,146 A | | 2/1978 | Howes |
| 4,265,249 A | | 5/1981 | Schindler et al. |
| 4,445,788 A | | 5/1984 | Twersky et al. |
| 4,573,968 A | | 3/1986 | Parker |
| 4,629,694 A | * | 12/1986 | Harpel ............................. 435/7.4 |
| 4,638,811 A | | 1/1987 | Bisera et al. |
| 4,643,712 A | | 2/1987 | Kulik et al. |
| 4,753,640 A | | 6/1988 | Nichols et al. |
| 4,762,130 A | * | 8/1988 | Fogarty et al. ................ 606/159 |
| 4,787,882 A | | 11/1988 | Claren |
| 4,808,158 A | | 2/1989 | Kreuzer et al. |
| 5,011,488 A | | 4/1991 | Ginsburg |
| 5,011,499 A | * | 4/1991 | Rathfelder et al. ............ 8/94.33 |
| 5,066,283 A | | 11/1991 | Skrabal |
| 5,078,135 A | | 1/1992 | Caprioli |
| 5,284,486 A | * | 2/1994 | Kotula et al. ................... 606/159 |
| 5,372,601 A | * | 12/1994 | Lary ............................... 606/159 |
| 5,472,417 A | | 12/1995 | Martin et al. |
| 5,531,714 A | | 7/1996 | Dahn et al. |
| 5,533,516 A | | 7/1996 | Sahatjian |
| 5,702,418 A | | 12/1997 | Ravenscroft |
| 5,769,821 A | | 6/1998 | Abrahamson et al. |
| 5,833,652 A | * | 11/1998 | Preissman et al. ............. 604/82 |
| 6,165,199 A | | 12/2000 | Barbut |
| 6,251,129 B1 | * | 6/2001 | Dobak et al. .................. 607/105 |
| 6,254,626 B1 | * | 7/2001 | Dobak et al. .................. 607/105 |
| 6,464,716 B1 | * | 10/2002 | Dobak et al. .................. 607/105 |
| 6,607,477 B1 | | 8/2003 | Longton et al. |
| 6,652,548 B2 | * | 11/2003 | Evans et al. ................... 606/159 |
| 7,179,232 B2 | | 2/2007 | Sutton et al. |
| 7,792,568 B2 | * | 9/2010 | Zhong et al. .................. 600/431 |
| 2002/0026174 A1 | | 2/2002 | Wallace |
| 2002/0091352 A1 | | 7/2002 | McGuckin et al. |
| 2002/0107479 A1 | | 8/2002 | Bates et al. |
| 2002/0107506 A1 | * | 8/2002 | McGuckin et al. .......... 604/523 |
| 2002/0128698 A1 | * | 9/2002 | Dobak et al. .................. 607/105 |
| 2002/0183815 A1 | * | 12/2002 | Nest et al. ..................... 607/105 |
| 2003/0060863 A1 | * | 3/2003 | Dobak, III ..................... 607/104 |
| 2003/0088299 A1 | * | 5/2003 | Magers et al. ................. 607/104 |
| 2003/0171664 A1 | | 9/2003 | Wendlandt |
| 2003/0208154 A1 | | 11/2003 | Close et al. |
| 2004/0082861 A1 | * | 4/2004 | Gruhl .................... A61B 1/3137 600/466 |
| 2005/0015048 A1 | * | 1/2005 | Chiu et al. ................ 604/101.04 |
| 2005/0038411 A1 | | 2/2005 | Okada |
| 2007/0232981 A1 | | 10/2007 | Ravenscroft et al. |
| 2009/0024057 A1 | | 1/2009 | Owen et al. |
| 2009/0184004 A1 | * | 7/2009 | Chatelier et al. ........... 205/777.5 |
| 2011/0212478 A1 | | 9/2011 | Owen et al. |

FOREIGN PATENT DOCUMENTS

| | | |
|---|---|---|
| JP | 54026783 | 2/1979 |
| JP | 62079069 | 4/1987 |
| JP | 2008545466 A | 12/2008 |
| WO | 2002083228 A2 | 10/2002 |
| WO | 2003080166 A1 | 10/2003 |
| WO | 2004010874 A1 | 2/2004 |
| WO | 2006/126002 | 11/2006 |
| WO | 2006126002 A1 | 11/2006 |

OTHER PUBLICATIONS

Office Action dated Aug. 30, 2011 in U.S. Appl. No. 11/920,632 (US 2009-0024057 A1).

Office Action dated Mar. 16, 2012 in U.S. Appl. No. 13/105,726 (US 2011-0212478 A1).

Office Action dated May 19, 2014 in U.S. Appl. No. 11/920,632 (US 2009-0024057 A1).

Office Action dated May 19, 2014 in U.S. Appl. No. 13/105,726 (US 2011-0212478 A1).

Office Action dated Sep. 25, 2012 in U.S. Appl. No. 11/920,632 (US 2009-0024057 A1).

Office Action dated Sep. 25, 2012 in U.S. Appl. No. 13/105,726 (US 2011-0212478 A1).

* cited by examiner

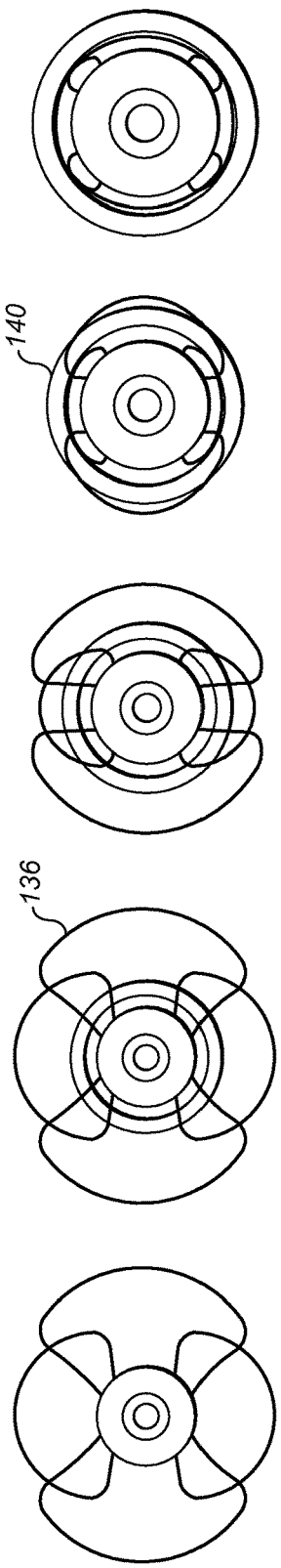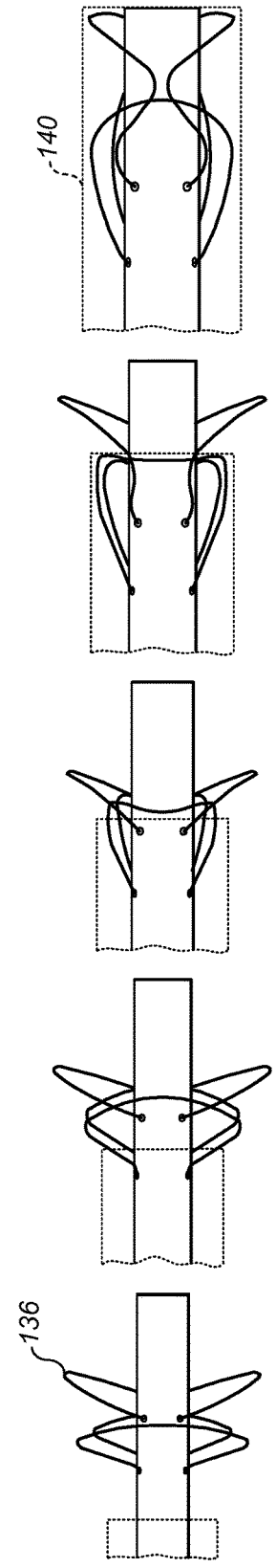

CATHETER

BACKGROUND TO THE INVENTION

The present invention relates to a catheter, in particular a catheter for collecting a plurality of samples from within a length of a blood vessel. The present invention further relates to associated methods, in particular a method for generating a data profile for one or more biomarkers emanating from the wall of a blood vessel, a method of profiling a length of a blood vessel to determine the pathological or physiological state of the blood vessel wall, and a method of sampling blood in vivo from a blood vessel.

It is known from WO 2006/126002 to take a plurality of samples of blood from along a length of a blood vessel. The samples are taken from near to the vessel wall and can be analysed so as to determine concentrations of biomarkers that are present there and hence to determine positions of vulnerable plaque, etc. along the blood vessel along the length of the sampling part of the catheter.

Although such earlier arrangements are very useful and effective, they present difficulties depending on the configuration of the catheter and the location and/or size of the vessel under test. For example, it is not always practical to manoeuvre a sample collection area of the catheter into position near to the vessel wall, due to the varying geometry of the vessel and constraints in positioning of the catheter. The present application seeks to obviate these difficulties and to improve the consistency of results and obtain closer correlation between the actual positions of sources of biomarkers and the positions at which those biomarkers are first sampled. As detailed below, this is achieved by inducing a flow from the boundary layer towards a sample collection area.

SUMMARY OF THE INVENTION

According to a first aspect of the present invention, there is provided a catheter for taking a plurality of samples from within a length of a blood vessel, the catheter including:

an elongate central body arranged to be inserted into and positioned along a blood vessel;

at least one collection area defined along the elongate central body for collecting samples at the central region of the blood vessel; and at least one mixer provided radially outwardly of the elongate central body and arranged to create a flow of blood from a boundary layer at a wall of the blood vessel to the elongate central body so as to enable the at least one collection area to collect samples from the boundary layer.

The at least one mixer preferably creates a flow of blood towards the collection area of the catheter so as to enable the at least one collection area to collect samples representative of fluid material present in the 360 degree radial section that defines the volume between the catheter and the inner wall of the blood vessel.

The collected samples can be representative of the entire cross sectional area of the blood within the vessel, i.e. from the centre of the elongate central body to the blood vessel wall.

By virtue of the at least one mixer, components such as biomarkers, emanating from as far away as the wall of a blood vessel and the adjacent boundary layer can be brought rapidly to the collection area along the elongate central body of the catheter for sampling. As a result, samples taken from a catheter (which has previously been placed in a blood flow) will more accurately reflect the actual position of the source of those components such as biomarkers. Also, as a result of bringing the flow to the at least one collection area more quickly and providing a shorter longitudinal offset between the actual source of biomarker and the sample site for the biomarker, detection becomes more accurate, precise and sensitive. Furthermore, the longitudinal offset becomes more consistent thereby allowing for appropriate correction.

The term boundary layer is used to cover all types of boundary layers including both velocity boundary layers and diffusive boundary layers.

Samples of blood extracted from the vessel may contain biomarkers which can be defined as any characteristic that is objectively measured and evaluated as an indicator of normal biologic or pathologic processes or pharmacological responses to a therapeutic intervention where the characteristics could include whole blood, cells, cellular components, chemicals and molecules such as lipids, proteins, nucleic acids and metabolic products.

Different types of mixer can be used, for instance brushes, sponges, foam, flaps, blades, paddles, helical sections, etc. However, preferably, at least one of the mixers is a static mixer.

This is advantageous, because a static mixer need not have any moving parts and can increase the rate of biomarker (or any blood component) diffusion across a wide range of flow conditions, from laminar to turbulent. Normally arterial flow is laminar and diffusion is very slow. A static mixer can be used to increase the diffusion of biomarkers, for instance by splitting the flow in two, with the resultant fluid elements being rotated by 90° in opposite directions to each other; and being recombined, the fluid elements having undergone a physical rotation relative to each other. Such a split, rotate and recombine process brings the biomarkers within the flow a step closer to the collection area. Repeating the process brings the biomarkers closer still and increases the effect of diffusion on fluid homogeneity.

Although it is possible to provide mixers which are relatively small in cross-section and, hence can be moved into position within a blood vessel in their normal state, preferably, the at least one mixer is deployable from an inactive state in which the at least one mixer is close to the elongate central body for insertion into a blood vessel and is deployable to a plurality of active states in which the at least one mixer is further away from the elongate central body so as to interfere with a boundary layer of the blood vessel.

In this way, in the inactive state, the catheter has an overall small cross-sectional area facilitating insertion into and along a blood vessel. The mixer is then deployable to its active state so as to better mix blood within the blood vessel.

The mixer may also engage (depending on the internal diameter of the vessel at that point) and conform to the wall of the artery. This can act to control the deployed diameter of the mixer in the absence of any other constraining force, for instance from a sheath.

Preferably, the mixer is able to deploy to an appropriate extent from the elongate central body so as to best interfere with the boundary layer which is along the wall of the blood vessel (such as artery) and potentially contains different concentrations (relative to the free stream or bulk flow of blood) of biomarkers emanating from the wall or absorbed into the wall as might be expected at locations of heterogeneous biological activity. For some diameters of blood vessel, this might mean that the mixer extends so as to meet with the wall of the blood vessel, whereas for larger diameter blood vessels, this might mean that the mixer moves to a position only close to the wall of the blood vessel.

Embodiments are possible where the at least one mixer extends on one side of the elongate central body. Depending on the nature of the mixer it may be desirable then to include at least one other mixer which extends on the opposite side of the elongate central body. However, preferably, the at least one mixer extends circumferentially around the elongate body in substantially all radial directions. In this way, it is possible for the mixer effectively to mix blood from any position of the periphery of the blood vessel. Preferably, the at least one mixer thus can create a flow of blood from the boundary layer around the entire periphery of the blood vessel.

Although the mixer can be embodied as a single component, the at least one mixer can comprise a respective plurality of mixing elements extending radially from the elongate central body.

It is possible for the plurality of mixing elements of the at least one mixer together to form an extent circumferentially around the elongate central body in substantially all radial directions.

Each mixing element could be fixed relative to the elongate central body. However, optionally each mixing element is pivotably attached to the elongate central body so as to pivot in the elongate direction of the elongate central body and towards and away from the elongate central body. In other words, each mixing element pivots about an axis perpendicular to the elongate direction or at least angled with that elongate direction.

In this way, in effect, each mixing element can be folded down to an inactive state resting against or close to an outer surface of the elongate central body. Alternatively, each mixing element can be pivoted up and away from the elongate central body to an active state. The extent to which mixing element is pivoted away from the elongate central body can be varied according to the diameter or internal extent of the blood vessel in which it is inserted.

Each mixing element could be formed from a respective component separate to the elongate central body and be mounted to the elongate central body by any appropriate pivoting mechanism. Alternatively, at least a portion of the mixing element at the point at which the mixing element is attached to the elongate central body is made of an appropriate flexible material.

Optionally, each mixing element has the form of a paddle extending in radial and tangential directions with respect to the elongate central body.

The paddle could be considered as a fin or flap which extends outwardly from the longitudinal surface of the elongate central body so as to disrupt blood flow in the blood vessel and cause mixing. Hence, the mixing element has a longitudinal extent which extends in at least partly a radial direction with respect to the elongate central body. On the other hand the lateral extent of the mixing elements extends in a direction parallel to tangents from the outer surface of the elongate central body.

It is possible for each mixing element to be angled relative to the longitudinal axis of the elongate central body so as to take the form of a blade of a propeller and to direct the blood flow in a predetermined circumferential or spiral direction according to the direction of angle.

Optionally, the mixing elements are arranged at successive positions along the elongate central body and, thus, are spaced apart longitudinally along the length of the elongate central body. At successive positions along the elongate central body, the mixing elements may be positioned at corresponding successive angles around the elongate central body.

In this way, when a mixing element at a first position along the elongate central body causes blood flow to be diverted circumferentially, subsequent mixing elements along the length of the elongate central body are positioned at different radial positions so as to interfere with different parts of the cross section of the blood vessel around the elongate central body. In particular, it is possible for the diverted flow from one mixing element to flow into the mixing element arranged at the next elongate position.

Optionally, the relative angle around the elongate central body between mixing elements at adjacent positions along the elongate central body is substantially 90°.

Thus, after each mixing element splits or diverts blood flow along the blood vessel, the next mixing element is offset by substantially 90° so as to divert a 90° offset portion of the cross-section of the blood vessel. This arrangement works particularly well with mixing elements having a radial extent of substantially 90°. For mixing elements having smaller radial extents themselves, the relative position between successive mixing elements can be a smaller radial angle. It is preferable for the radial extent of the mixing elements to slightly exceed the radial angle therebetween, so that there is some overlap of successive mixing elements when viewed axially.

Optionally, the mixing elements are arranged in pairs, each pair of mixing elements being positioned at a respective position along the elongate central body and individual mixing elements of a pair of mixing elements being on opposite respective sides of the elongate central body. In other words, a pair of mixing elements might include one mixing element extending above an elongate central body and another mixing element extending below the elongate central body. Where successive mixing elements are at corresponding successive angles, the next pair of mixing elements could have one mixing element extending to one side of the elongate central body and the other mixing element extending to the other side of the elongate central body.

It is possible to use only one pair of mixing elements. However, optionally, the at least one mixer includes at least two such pairs of mixing elements.

This provides a good compromise between providing an excessive number of mixing elements and giving sufficient mixing.

Additional pairs of mixing elements could be provided to further increase the quality of mixing. Certainly, good results can be achieved with 3, 4 or 6 pairs.

In order to place the mixer in the inactive state, it is possible to deflect each of the mixing elements so as to be substantially flat against the outer surface of the elongate central body. Preferably the mixing elements are shaped and spaced such that when they are deflected in this way, mixing elements at adjacent positions along the elongate central body substantially do not overlap. With this arrangement, the profile of the catheter is minimised, thus improving movement of the catheter to a target site.

It is also possible to arrange for outer portions of the mixing elements to be thinned or profiled such that the overlapping of adjacent mixing elements does not take up undue radial depth.

The collection areas can be arranged in any known or appropriate manner for collecting samples. However, the at least one collection area includes at least one collection port located at a respective position along the elongate central body for collecting a respective sample at that position. Samples collected at that position will, of course, be in effect a sample collected from the boundary layer prior to mixing.

It is possible to provide catheters with a variety of different arrays of mixers and collection areas. For example, a plurality of collection areas can be provided for each mixer. Similarly, each collection area could include a plurality of collection ports. However, in a preferred embodiment, a single collection port is provided between adjacent mixers. A collection port may be provided at a position upstream of any mixing so as to provide a sample of unmixed blood to be analysed for purposes of normalization.

The collection ports may provide ports for sampling in any known or appropriate manner, for instance opening to sampling pockets which might optionally include absorbing material. However, in one embodiment the elongate central body includes at least one lumen extending internally along the elongate central body connecting with the at least one collection port.

The lumen forms a volume into which a sample of blood may flow from the respective collection port. The lumen can be pre-filled with saline or equivalent. Natural blood pressure may be used in order to allow a sample to be collected in the lumen. Alternatively, low pressure may be applied to an opposite end of the lumen so as to draw blood in through the respective collection port. The lumen may be coated with anticoagulation materials, e.g. heparin, phosphorylcholines.

Optionally, the elongate central body includes a plurality of lumens extending internally along the elongate central body connecting with respective collection ports. In this way, a plurality of samples, for instance one sample between each mixer, can be taken at the same time.

In order to reduce the mixing requirements for the mixers, it is possible to use mixers which merely create a flow of blood from a boundary layer to the elongate central body without necessarily mixing blood throughout the entire cross-section around the elongate central body. This means that blood flow from a boundary layer at one side of a blood vessel may only be presented to that same side of the elongate central body. To ensure that samples of this blood flow are taken, it would be possible to provide a plurality of collection ports around the periphery of the elongate central body. However, in one embodiment, at the at least one collection area, the elongate central body includes an outer wall having an outwardly facing surface and an inwardly facing surface and an inner body in which the at least one collection portion is defined. The inwardly facing surface of the outer wall and the inner body can define a circumferential gap therebetween. A circumferential array of through holes can be defined through the outer wall between its inwardly facing surface and its outwardly facing surface. The circumferential gap can then form a manifold for feeding the at least one collection port from a plurality of radial directions.

In other words, a flow of blood from the boundary layer at any position around the periphery of the blood vessel will be provided to the elongate central body. By providing the through holes spaced around the entire periphery of the elongate central body, it should always be possible, by means of at least one of those through holes, to take a sample of the blood flow to include samples representative of the 360 degree segment around the catheter.

Because the through holes are all connected to the collection port by means of the manifold, the collection port is thus able to collect an appropriate sample, even if the blood flow from the boundary layer is provided to an opposite side of the elongate central body to that of the collection port.

Optionally, the catheter is provided with a sleeve within which the elongate central body and the at least one mixer can be stowed. By withdrawing the sleeve the at least one mixer and the at least one collection area can be exposed.

In one embodiment, exposing the at least one mixer allows that mixer to move from its stowed inactive state to a deployed active state. Preferably, by moving the sleeve back over the elongate central body the mixers can be moved back to their stowed inactive state.

According to a second aspect of the present invention, there is provided a method for generating a data profile for one of more biomarkers emanating from the wall of a blood vessel, which method comprises analysing a plurality of blood samples from a bloodstream that has been mixed substantially across the radial extent of the blood vessel to include blood present in the boundary layer at the blood vessel wall, the blood samples being taken at respective locations along a length of the blood vessel, the analysis including the steps of:

measuring a concentration level of a biomarker in each blood sample;

determining a first concentration correction factor for each respective blood sample to correct for differences in sample volume and dilution between different blood samples;

determining a second concentration correction factor to correct for a measured background concentration level for the biomarker present in general circulation within the bloodstream;

for each blood sample, applying a respective first and the second concentration correction factor to the measured concentration level of the biomarker in each blood sample to determine a corrected concentration level of the biomarker; and, generating a data profile of corrected concentration levels for the biomarker along the length of the blood vessel.

Optionally, the method further comprises the step of analysing at least one blood sample collected from an upstream location to determine the second correction factor to be applied to the measured concentration levels of the biomarker.

Optionally, blood samples are analysed to measure the concentration of a reference marker in general circulation in the bloodstream having a known or measured concentration, whereby a respective first correction factor is calculated for each blood sample to correct for differences between the measured concentration of the reference marker in the blood sample and that in general circulation.

Optionally, blood samples are taken from within a coronary artery and at least one blood sample taken from an aortic arch.

According to a third aspect of the present invention, there is provided a method of profiling a length of a blood vessel to determine the pathological state or physiological state of the blood vessel wall, comprising the steps of:

introducing into a blood vessel a flexible vascular catheter having a body section provided with a plurality of blood collection ports for collecting samples along a length of the blood vessel;

deploying at least one mixer radially outwardly of the catheter body, the mixer thereby mixing blood substantially across the radial extent of the blood vessel to include blood present in a boundary layer at the blood vessel wall;

collecting blood at the blood collection ports downstream of the at least one mixer;

analysing blood collected by the blood collection ports of the catheter to determine a data profile of the concentration levels of one or more biomarkers along the length of the blood vessel.

According to a fourth aspect of the present invention, there is provided a method of sampling blood in vivo from a blood vessel, comprising the steps of:

introducing into a blood vessel a flexible catheter having a body section provided with a plurality of blood collection ports for collecting samples along a length of the catheter;

deploying at least one mixer radially outwardly of the catheter body, the mixer thereby mixing blood flowing within the blood vessel substantially across the radial extent of the blood vessel; and, collecting blood at one or more blood collection ports positioned downstream of the mixer for subsequent analysis.

BRIEF DESCRIPTION OF THE DRAWINGS

The invention will be more clearly understood from the following description, given by way of example only, with reference to the accompanying drawings, in which:

FIGS. 13(a) to (e) illustrate folding of wire structures for use with the present invention;

FIGS. 14(a) to (e) illustrate the folding wire structures of FIGS. 13(a) to (e) from a different view;

DETAILED DESCRIPTION

The present invention concerns the provision of at least one mixer on a catheter for taking samples within a blood vessel. The at least one mixer is for creating a flow of blood from outer portions of the blood vessel to an inner central region of the blood vessel where samples can be collected by the catheter. For example, a plurality of samples may be taken along a length of a blood vessel such as a coronary artery, and those samples analysed to detect biomarkers and thereby identify vulnerable plaques and other phenomena releasing biomarkers into the blood flow of the blood vessel. Such phenomena might be damaged epithelial tissue, healed epithelial tissue and in general any localised process in which biological or pharmacological processes are underway e.g. tissue response to stenting, measures of drug uptake from drug releasing stents, tissue response to balloon angioplasty, stent grafting and any other natural process or interventional procedure that might cause a localised tissue response. In particular, it is desirable to create a flow from the boundary layer at the wall of the blood vessel to the central region of the blood vessel. In this way, biomarkers resulting from plaque from the walls of the blood vessel can be sampled and detected by the catheter irrespective of the radial location of the catheter within the blood vessel.

Figure 1:
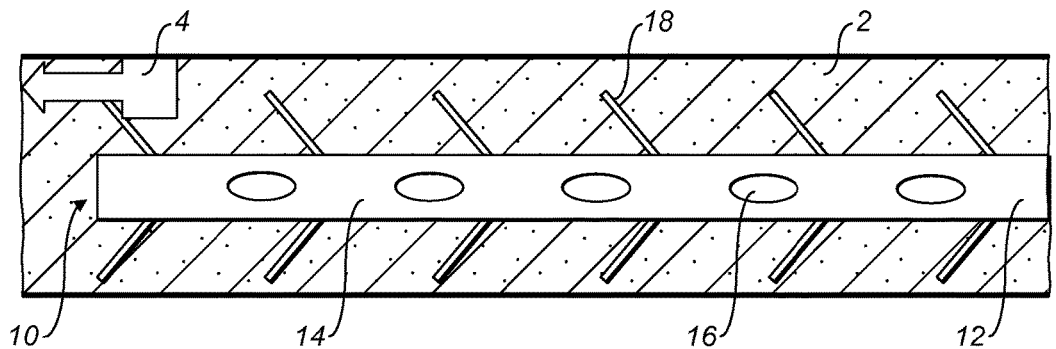
FIG. 1 illustrates schematically an embodiment of the present invention.

FIG. 1 illustrates schematically a length of a blood vessel 2 into which a catheter 10 has been inserted. The catheter 10 includes an elongate central body 12 having a plurality of collection areas 14 along its length. In this illustrated embodiment, each collection area 14 includes a respective collection port 16 for collecting an individual sample. However, the collection areas 14 may alternatively be embodied with other known means of taking samples, or indeed may include more than one collection port for collecting respective samples.

As illustrated, a plurality of mixers 18 is also provided along the length of the catheter 10. In particular, the mixers are provided radially outwardly of the elongate central body 12. The mixers 18 extend in a region of the blood vessel 2 at least close to the outer wall of the blood vessel 2 and the boundary layer at that wall.

It is sufficient to have only one mixer 18 upstream of a plurality of collection areas 14. However, with each additional mixer, mixing of the blood within the blood vessel 2 is improved such that the results of sampling at the central region of the blood vessel can also be improved. Hence, it is desirable to provide a plurality of mixers 18 and these are most advantageously distributed alternately between adjacent collection areas such that each successive collection area is sampling a better mixed volume of blood.

FIG. 1 illustrates a biomarker release stream 4, for instance resulting from plaque on the wall of the blood vessel 2. Biomarkers released into the boundary layer will tend, if undisturbed, to remain in that boundary layer such that optimal sampling by a catheter with collection areas in the central region of the blood vessel 2 can be difficult to achieve.

It is possible that the catheter (for instance on a guidewire) is off-centre. As will become apparent below, the mixers can have a second function of biasing the catheter to the centre of the blood vessel (for instance by their inherent resilience/stiffness acting against any off-centering force of a guidewire).

With a structure such as illustrated in FIG. 1, where a plurality of successive mixers 18 is provided, it is far from essential that each mixer provide 100% mixing. It will be appreciated that for a mixer 18 having 50% efficiency, the mixed portion of blood at successive collection areas will be mixed by percentages of 50, 75, 87.5, 93.8, 96.9, 98.4. Similarly, for mixers with efficiencies of 75% mixing will occur with percentages of 75, 93.8, 98.4, 99.6, 99.9, 100 and for mixers of 90% efficiency with percentages of 90, 97.5, 99.4, 99.8, 100, 100.

By taking these mixing proportions into account, it will be possible to predict where, along the length of the catheter 12, the biomarker release stream 4 emanates from. Of course, where the biomarker release stream 4 and its associated plaque are positioned somewhere along the length of the catheter 12, collection areas 14 upstream of the biomarker release stream will not sample any biomarker at all (or at least will only sample a background level).

In one embodiment, a collection area is provided upstream of any mixer 18 such that an unmixed sample of the blood can be taken so as to provide an indication of any background levels. The additional upstream collection area is highly advantageous in performing normalisation of data acquired from the samples.

The schematically illustrated mixers 18 of FIG. 1 can be embodied in many different ways, for instance as lamina flow static mixers or turbulent mixers. A static mixer is a mixer that achieves its mixing by staying still. It does not add energy to the system. It may work on both laminar or turbulent flow. A mixer that acts upon turbulent flow may include a static mixer and requires that there is sufficient energy within the flow to generate turbulent recirculation. In a mixer that induces turbulence as the core mechanism for mixing, it may do this by shearing the liquid or adding energy in the form of a secondary flow or powered moving element. Preferably, the static mixer is optimised for laminar flow mixing but ideally operates for all types of flow, i.e. laminar, and turbulent (best defined as Reynolds Numbers from 1×10−6 to 10,000). The term laminar and turbulent is complex here as a turbulent flow may actually be considered laminar if the analysis scale is changed, i.e. a turbulent flow path can be considered as being made up of lots of laminar sections going in different directions. Hence, at the scale of coronary arteries, although the pulses from the heart may be considered "turbulent", the net flow characteristic within that artery is best considered as being laminar.

Irrespective, in some embodiments, the mixers are deployable from a first stowed and inactive state to a second deployed and active state. In particular, in some embodiments, the mixers 18 start in a stowed inactive state in which they are close to the outer surface of the elongate central body 12 such that the overall cross-sectional area presented by the catheter 10 is relatively small. This allows the catheter 10 to be inserted into the blood vessel 2 more easily. Once the catheter 10 has been inserted into the desired region of the blood vessel 2, the mixers 18 are then moved to their deployed and active state. In this state, the mixers 18 extend outwardly toward the outer regions of the blood vessel 2 and the overall cross-sectional area presented by the catheter 10 is increased.

Figure 2:
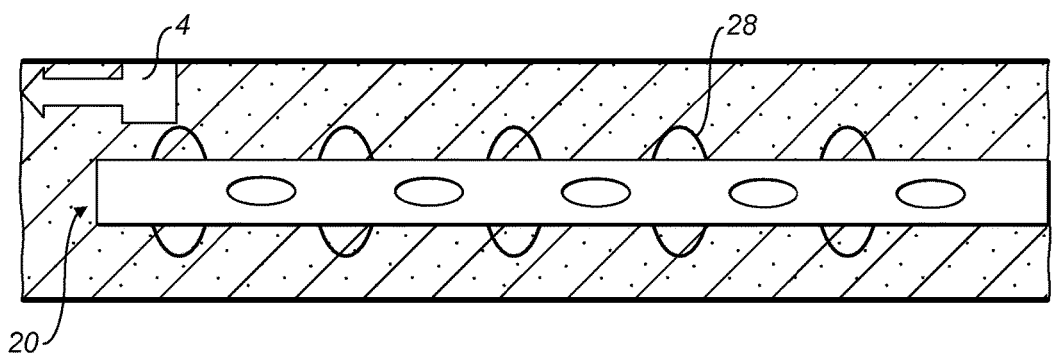
FIG. 2 illustrates schematically an alternative embodiment.

It is possible to form a mixer from foam and FIG. 2 illustrates schematically a catheter 20 having deployed foam mixers 28.

Figure 3:
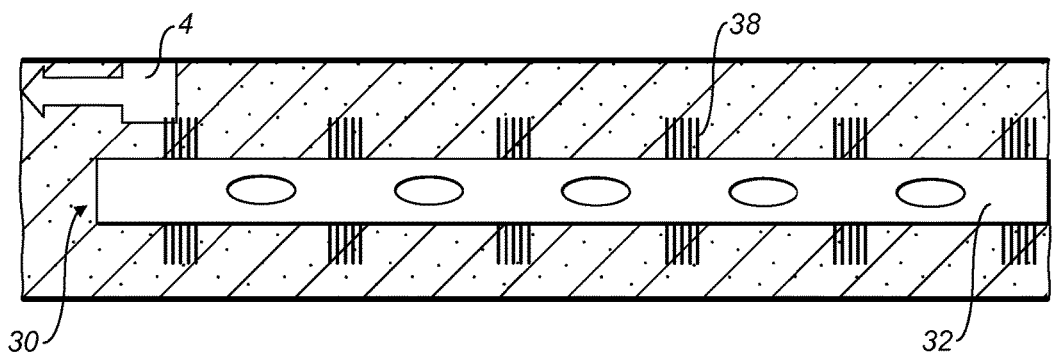
FIG. 3 illustrates schematically an alternative embodiment.

FIG. 3 illustrates schematically an arrangement in which a catheter 30 uses mixers 38 constructed from a plurality of fibres or bristles. The fibres or bristles extend radially from the elongate central body 32.

It is preferable that mixers are able to operate within blood vessels of a variety of different internal diameters. In this respect, it is desirable that the deployed state of the mixers extends over a range of diameters. For smaller diameter blood vessels, the mixers 18, 28, 38 extend from the elongate central body 12, 22, 32 and touch the wall of the blood vessel 2. To attain the desired mixing, it is sufficient for the mixers to extend to a region close to the wall of the blood vessel 2 and merely interfere with the boundary layer. Blood vessels are not uniformly sized and may be tapered. It is desirable for the catheter to be able to function along the length of a blood vessel, irrespective of the internal diameter. Hence, by using deployable mixers, the mixers may be deployed to differing extents to touch or extend close to the wall of the blood vessel no matter what the internal diameter of the blood vessel at that point, within a certain range.

In certain arrangements, the mixers provide the desired mixing irrespective of the direction of flow. Also, where the mixers are bent over from the elongate central body towards the walls of the blood vessel, it will be appreciated that they will be angled towards or away from the direction of flow. Indeed, with the mixers in a deployed state such that their distal ends, or tips, meet with the walls of the blood vessel, if the elongate central body is moved within the blood vessel, it is possible for the mixers to be deflected such that they move between states facing towards and facing away from the direction of flow. In view of this, preferred arrangements of the mixers operate for mixing the flow irrespective of whether the mixers face into the fluid flow or face away from the fluid flow.

Certain embodiments of the present invention use static mixers, these offering the best potential for meeting size, deployment, mixing and manufacturability requirements.

It is desirable to provide complete mixing whereby any biomarker propagates both about the circumference and radially through the bulk blood flow in the blood vessel.

In other fields of technology, fluid mixers have been proposed using a series of helical sections, each helical section having an opposite direction of twist with respect to the adjacent helical section.

Figure 4A:
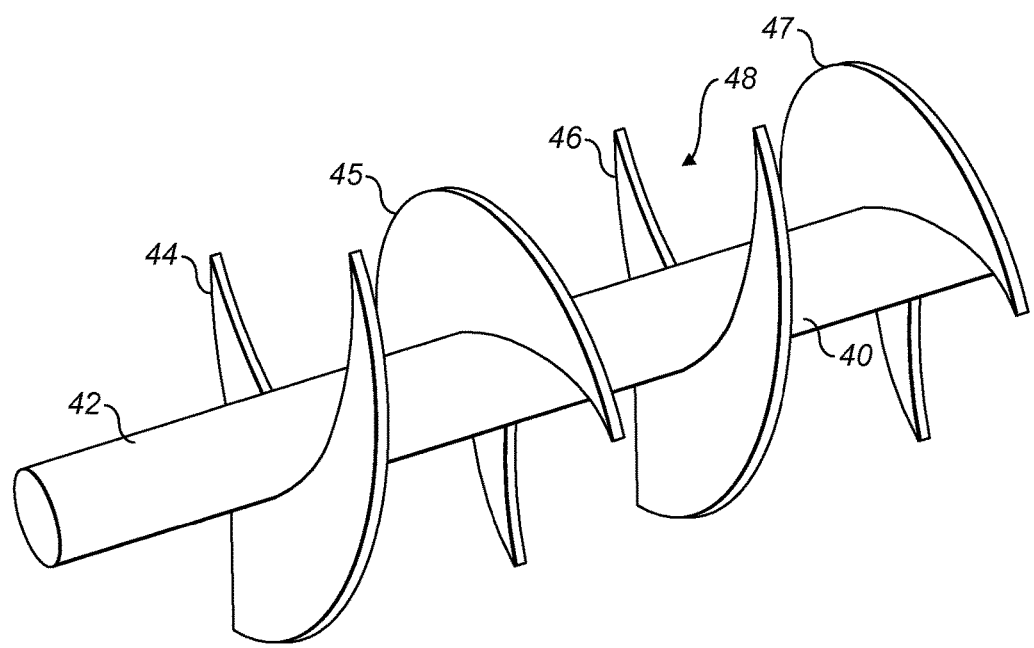
FIGS. 4(a) and (b) illustrate schematically alternative embodiments.

FIGS. 4(a) and (b) illustrate two possible arrangements for static mixers.

Each of the mixers of FIGS. 4(a) and (b) include a plurality of mixing elements which extend radially from the elongate central body.

In the mixer 48 of FIG. 4(a) four mixing elements 44, 45, 46 and 47 are arranged along the length of the elongate central body 42 of the catheter 40. Each mixing element 44, 45, 46, 47 has a helical and screw shape so as to rotate the flow of fluid as it moves in the longitudinal section of the elongate central body 42. As illustrated, each mixing element rotates through 360° and each mixing element rotates in an opposite direction to any mixing element adjacent to it. In this way, while one mixing element causes fluid flow to rotate in one direction, when that fluid flow reaches the next mixing element, the fluid is caused to change its flow and flow in the opposite direction. It will be appreciated that any number of mixing elements could be used as a mixer 44 but that preferably two or more mixing elements are used. It should also be appreciated that other arrangements could use similar mixing elements which rotate through more or less than 360°.

Figure 4B:
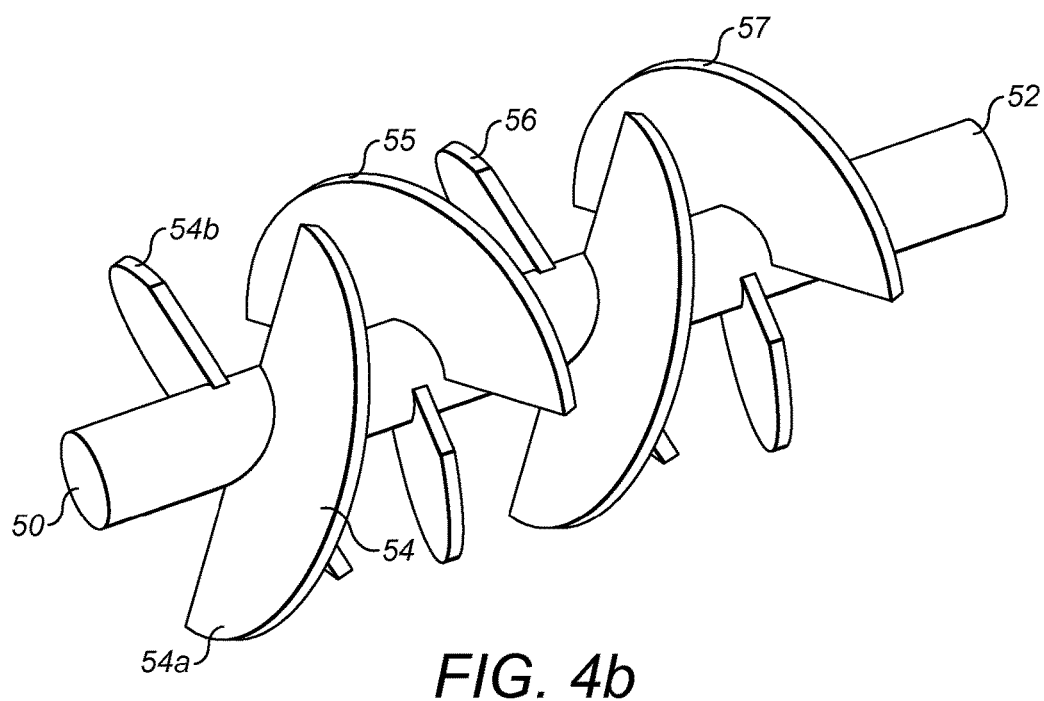

In certain arrangements such as illustrated in FIG. 4(*a*), the outward flow of fluid from one mixing element is directed towards a surface of the mixing element of the next mixing element. In the illustrated embodiment of FIG. 4(*a*), this is achieved by one set of alternate mixing elements 44, 46 being rotationally offset relative to the other set of alternate mixing elements 45, 47 by 90°.

In the arrangement of FIG. 4(*b*) the mixing elements 44, 45, 46, 47 of the arrangement of FIG. 4(*a*) are replaced by pairs of mixing elements 54, 55, 56 and 57.

In the arrangement of FIG. 4(*b*), a helical, spiral or screw section is replaced by two diametrically opposed, but relatively angled planar sections. Considering the pair of mixing elements 54, a first mixing element 54*a* extends from one side of the elongate central body 52 of the catheter 50 in the form of a 180° sector for filling half of the internal space of a blood vessel. The first mixing element 54*a* passes through a diameter of the elongate central body 52, but is angled relative to a plane perpendicular to the axis of the elongate central body 52. On the other hand, the second mixing element 54*b* of the pair of mixing elements 54, while similarly being a sector passing through the diameter of the elongate central body 52 is angled oppositely to the plane perpendicular to the axis of the elongate central body 52. In this way, the pair of mixing elements 54 functions crudely like a 360° spiral or helix. Preferably, at least one of the first and second mixing elements 54*a*, 54*b* is in the form of a sector just over 180° so that there is some overlap of the pair of mixing elements when viewed axially.

As with the embodiment of FIG. 4(*a*), it is preferable that the outlet of flow of one pair of mixing elements 54 flows into an opposing face of the next pair of mixing elements 55. Hence, as illustrated in FIG. 4(*b*), alternate pairs of mixing elements 54, 56 are arranged with respect to the other set of alternate pairs of mixing elements 55, 57 at an offset angle of 90° about the axis of the elongate central body 52.

Figure 5:
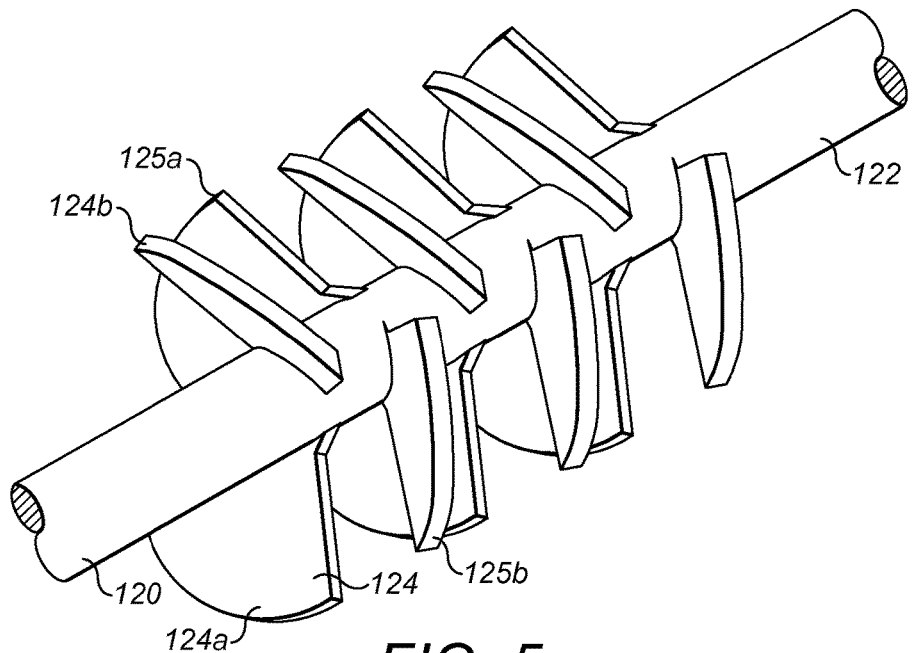
FIG. 5 illustrates a preferred embodiment of the present invention.

FIG. 5 illustrates a further arrangement where the mixing elements are arranged in pairs. However, in the arrangement of FIG. 5 the individual mixing elements of the pairs of mixing elements are arcuate sectors of less than 180°. The mixing elements are still effective in causing rotation of the flow of fluid around the catheters and for causing opposing counter-rotation at different portions of the mixer along the length of the catheter.

FIG. 5 illustrates a non-helical mixer. The mixing elements, or fins, are not tilted relative to the axis of the elongate central body (other than being slightly folded in).

As discussed above, it is desirable for the mixers to be deployable from stowed positions close to the elongate central body of the catheter to deployed positions extended outwardly away from the elongate central body towards the outer periphery of a blood vessel.

By constructing the mixing elements of FIGS. 4(*a*) and (*b*) and of FIG. 5 from appropriate materials at least where they are attached to the elongate central body, it is possible for those mixing elements to be folded down against the outer surface of the elongate central body. However, it is desirable to be able to stow the mixers in a more compact manner than is possible with these arrangements. It will be appreciated that the extent of the mixing elements of the arrangements of FIGS. 4(*a*) and (*b*) means that the mixing elements themselves need to deform in order to be folded against the outer surface of their corresponding elongate central bodies.

Figure 6:
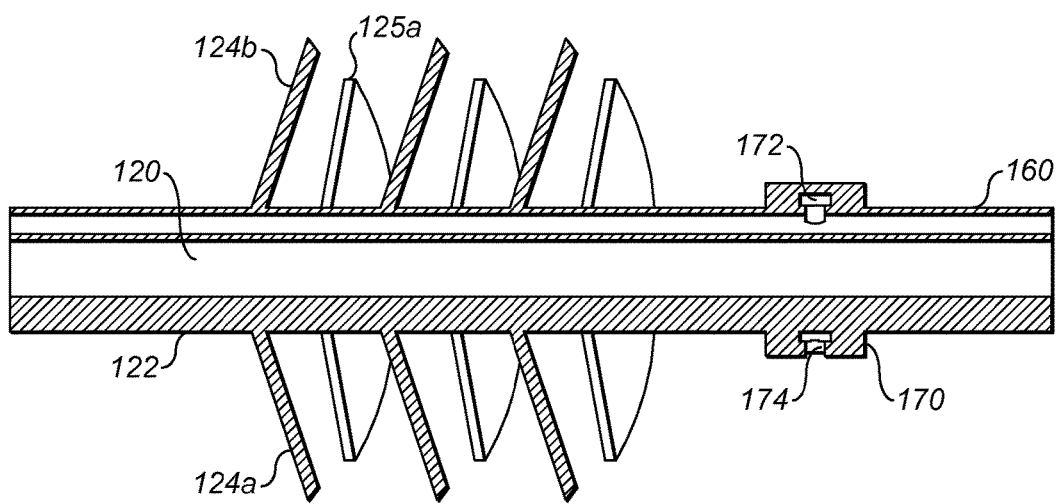
FIG. 6 illustrates an embodiment similar to FIG. 5 in cross-section.

FIG. 5 illustrates one embodiment of the present invention allowing good mixing and effective stowage of the mixers before deployment. FIG. 6 essentially illustrates the arrangement of FIG. 5 in cross-section, but is in conjunction with a collection port of a type to be described in greater detail below, in particular with reference to FIG. 20.

As illustrated, the mixing elements are arranged in pairs, with individual mixing elements 124*a*, 124*b* of a pair 124 being arranged on opposite sides of the elongate central body 122 of the catheter 120. The individual mixing elements extend radially and circumferentially from the elongate central body 122 and form paddles or fins which are to extend to the internal outer periphery of a blood vessel. The mixing elements take the form of sectors of relatively small angular extent, for instance in the region of 90°. Each individual mixing element may be generally planar and follow a plane extending through a diameter of the central elongate body 122. In an at rest state, opposing mixing elements of a pair of mixing elements may extend outwardly perpendicular to the axis of the elongate central body 122 and lie in a common plane. FIG. 5 illustrates the mixing elements deflected in one longitudinal direction, whereas FIG. 6 illustrates those mixing elements deflected in an opposite longitudinal direction.

In the illustrated embodiment, adjacent pairs of mixing elements extend from the elongate central body 122 in different radial directions. In the illustrated embodiment alternate pairs of mixing elements extend in one radial direction, whereas the interleaved pairs of mixing elements extend in a different radial direction, preferably at 90° to the first alternate set of mixing elements. Thus, in the cross-section of FIG. 6, cross-section through opposing mixing elements 124*a* and 124*b* are visible, whereas mixing element 125*b* is not visible and only mixing element 125*a* is visible behind the elongate central body 122.

The advantage of the arrangement of FIGS. 5 and 6 is that the individual mixing elements are able easily to be folded along the length of the elongate central body 122 and wrapped partly around its periphery.

It will be appreciated that, although the embodiment of FIGS. 5 and 6 includes six pairs of mixing elements, with individual mixing elements having a radial extent of appropriately 90° and alternate pairs of mixing elements angled relative to one another by appropriately 90°, other similar arrangements are possible using mixing elements of different angular extent, using different numbers of mixing elements in any one group and using a different number of groups of mixing elements along the length of the elongate central body 122. In this regard, it is preferable for the radial extent of at least one of the mixing elements to slightly exceed the radial angle between the alternate pairs, so that there is some overlap of the mixing elements of successive alternate pairs when viewed axially. For example, a mixing element having a sector of 100° could be appropriate for this arrangement.

The arrangement allows there to be provided a deployable static mixer including at least two mixing elements that remain fixed within a blood vessel so as to sequentially separate, rotate and re-combine fluid flow and so as to effect mixing across the radius of the blood vessel. Because of the symmetry of the arrangement, this will work with a fluid flow in either direction. Also, this will work with varying degrees of mixing element angle, in other words the extent to which the mixing elements are folded down towards the elongate central body 122. The sequentially placed groups of mixing elements induce counter-rotating flows within the bulk fluid flow. By attaching the mixing elements to the elongate central body 122 and hinging them near the axis of the elongate central body 122 and the blood vessel, the mixing elements may be folded to adapt the mixer to a range of blood vessel diameters. In other words, for small blood vessel diameters, the mixing elements will be angled over towards the elongate central body 122, but, for larger blood vessels, the mixing elements may extend directly out from the elongate central body 122, perhaps not contacting the walls of the blood vessel, but merely interfering with the boundary layer against those walls.

With the mixing elements folded against the elongate central body, a concentric sheath or sleeve may be arranged around the catheter 120. The sheath or sleeve may be withdrawn from the catheter 120 so as to expose the mixing elements and allow the mixing elements to deflect outwardly from a stowed position to an active position. After the catheter has been used, the sheath or sleeve can then be pushed back over the mixing elements causing them to deflect back towards the elongate central body 122 and fit within the sheath or sleeve in their stowed positions.

In one embodiment, the mixing elements function whether or not they face into or away from the fluid flow. Therefore, how the mixing elements emerge from the sheath or sleeve is not important to functioning of the mixer. Indeed, if the catheter 120 is moved axially within a blood vessel such that the mixing elements are caused to be deflected between an orientation angled into or away from the fluid flow to the other of into or away from the fluid flow, functioning of the mixer is not impeded.

In one embodiment, the mixing elements are flexible. Thus, optionally, the mixing elements are made with sufficient elasticity to provide the necessary combination of both resilience and compliance to enable safe and effective use within a blood vessel. Optionally, this ensures that the outermost diameter of the mixing element, when deployed, makes a close fit with the outermost diameter of the blood vessel without damaging it or at least comes close to the wall of the blood vessel so as to interfere with its boundary layer. In addition, as mentioned above, such deployable mixing elements may, due to their resilience, act to urge the catheter into a central position within the blood vessel.

The mixer elements can be constructed in a variety of different ways using a variety of different materials while still meeting the basic requirements of the invention. It is preferred for the mixing elements to be able to deploy and function in blood vessels having internal diameters in the range of 2.3 to 4.0 mm, and more preferably 2.0 to 5.0 mm.

Optionally, the mixing elements are made from materials that provide sufficient resistance to allow the mixing elements to deploy (for instance upon retraction of a sheath) by expanding (in the manner of bending outwardly from the elongate central body) until the mixing element reaches full deployment or, alternatively, contacts the inner wall of the blood vessel. Optionally, the mixing elements are made from materials that, once deployed, exert a stiffness appropriate to resist the flow of blood. However, they should be soft enough not to abrade or damage the endothelial layer (inner wall) of the blood vessel. Optionally also the mixing elements are made from materials that enable the mixer to be collapsed when subjected to a collapsing force by the operator, for instance moving a sheath or sleeve over the deployed mixing elements and driving them to their stowed state.

Suitable materials are preferably bio-compatible and include medical grade elastomeric materials such as silicones, urethanes, thermoplastic vulcanizates, etc. It is also possible to use non-elastomeric medical grade materials by controlling their geometry, for instance, their cross-sectional area, to provide the appropriate stiffness characteristics. Materials that can be injection molded, cast, solid freeform fabrication (inkjet, SLA, etc), machined or deposited can be used to make the mixing elements.

Figure 7:
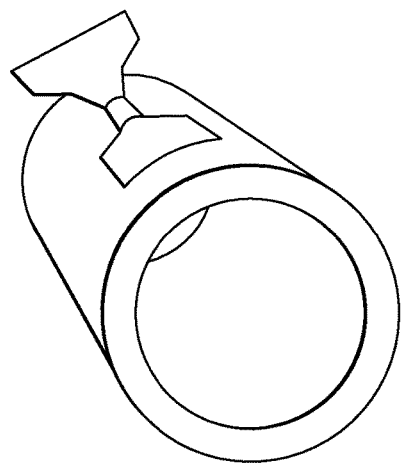
FIG. 7 illustrates schematically a mixing element for use with the present invention.

The mixing elements can be formed from single materials, such as molded elastomers, or may be cut and bent from a metal tube for instance made from a shape memory metal or polymer (for example nitinol). In this regard, FIG. 7 illustrates a fin profile cut into the wall of a tube and then folded out to form a fin or paddle forming a mixing element.

Figure 8:
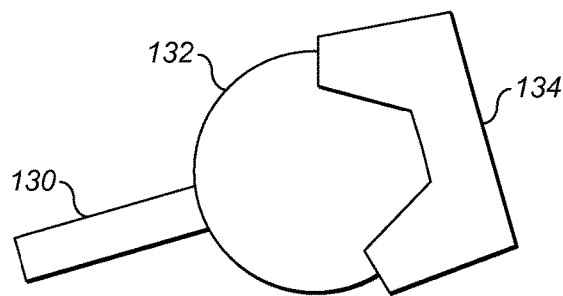
FIG. 8 illustrates schematically an alternative mixing element for use with the present invention.

Mixing elements can also be made as a composite, with different materials used for different parts of the mixing element. FIG. 8 illustrates a root, mast or scaffold 130, for instance made from wire, such as flexible or shaped memory or super elastic wire. This connects the main body 132 of the mixing element to an elongate central body of the catheter. The main body 132 may be made from a different material, in particular that can conform to the circumference of a tube. It may be provided with a tip 134 constructed from a very soft elastomer to minimise any damage to a blood vessel wall. The main body or sail can be molded, cast or stamped.

Figure 9:
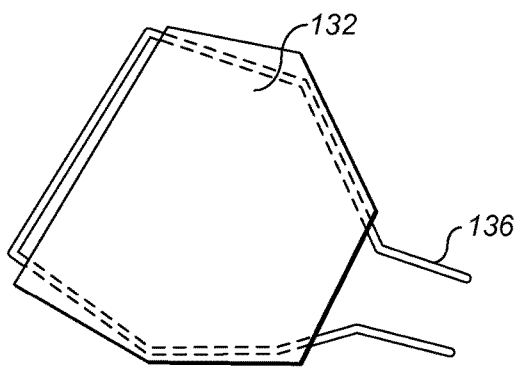
FIG. 9 illustrates schematically an alternative mixing element for use with the present invention.

FIG. 9 illustrates an arrangement where a main body 132 is formed from a polymer film wrapped around a scaffold 136 which extends to form the root or mast and preferably has shaped memory and forms a super elastic wire frame or scaffold.

Figure 10:
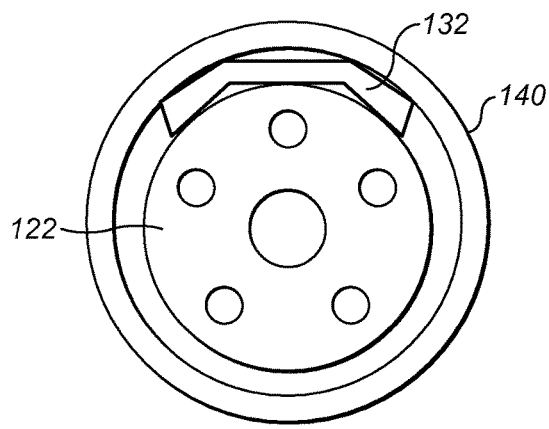
FIG. 10 illustrates schematically a mixing element folded in a stowed position.

FIG. 10 illustrates schematically the main body 132 of a mixing element in its stowed state and positioned between an elongate central body 122 and an outer sheath 140. As illustrated, the flexible structure of the mixing element allows it to conform to the outer surface or wall of the elongate central body 122.

Figure 11:
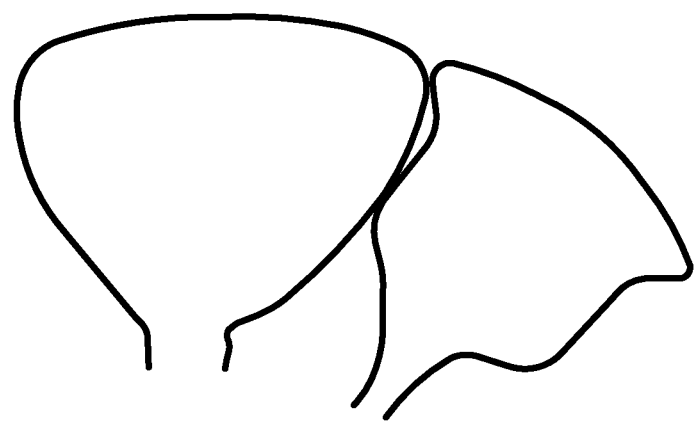
FIG. 11 illustrates schematically mixing elements stowed adjacent one another.

Following on from FIG. 10, it will be appreciated that, in some embodiments, different mixing elements do not overlap with each other. In this respect, it is possible to use profiled edges, such as illustrated in FIG. 11 to prevent overlap of mixing elements when the mixing elements are collapsed against the outer surface of the elongate central body.

Figure 12:
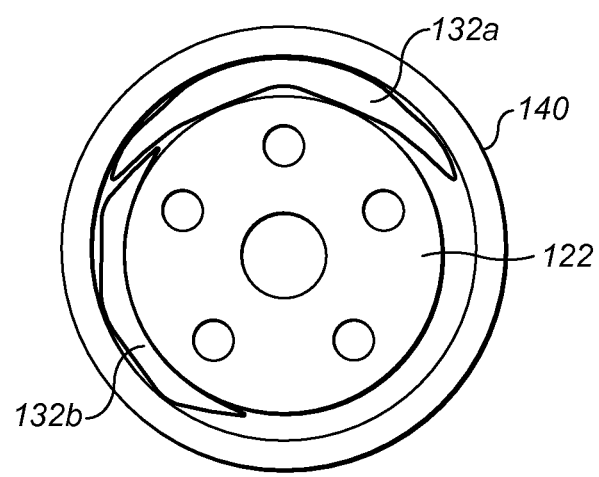
FIG. 12 illustrates schematically two mixing elements folded together.

It is also possible to use variable fin thickness to minimise the total thickness of the mixing elements when sheathed. For instance, as illustrated in FIG. 12, a thinner fin profile is provided in the regions of overlap of the mixing elements 132a and 132b.

FIGS. 13(a) to (e) and 14(a) to (e) illustrate a wire structure such as mentioned with reference to FIG. 9. A deployed state is illustrated in FIGS. 13(a) and 14(a). Successive Figures move to a fully stowed state within a sheath as illustrated in FIGS. 13(e) and 14(e). FIGS. 13(a) to (e) illustrate an end view of a catheter with wires 136 and sheath 140 whereas FIGS. 14(a) to (e) illustrate a side view of the catheter with wires 136 and sheath 140.

As illustrated, each wire structure 136 is able to fold into the sheath 140 by collapsing the wire structure 136 in front of it. As described above with reference to FIG. 9, the wires can act as a frame to a flexible thin film and hence act as the mixing elements.

Various possibilities exist for constructing the catheter with the mixing elements.

The mixing elements could be formed separately and then individually stuck to the outer wall of the elongate central body. For example, adhesives, thermal bonding, shrink fitting or ultrasonic welding could be used to attach the mixing elements to the elongate central body.

Each mixer could be formed as an individual unit including all of its mixing elements. For example, a mixer, including the mixing elements could be over molded onto a pin of appropriate diameter, then removed and adhered to the elongate central body.

Figure 15:
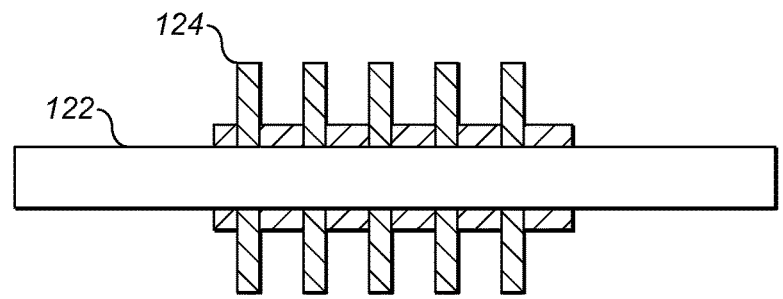
FIG. 15 illustrates schematically an example of constructing a mixer.

FIG. 15 illustrates schematically a plurality of mixing elements 124 being over molded onto tubing 122. As illustrated, the mixer is being over molded directly onto the elongate central body 122, but similarly the mixer could be molded onto a forming pin and then transferred to the elongate central body 122.

Figure 16:
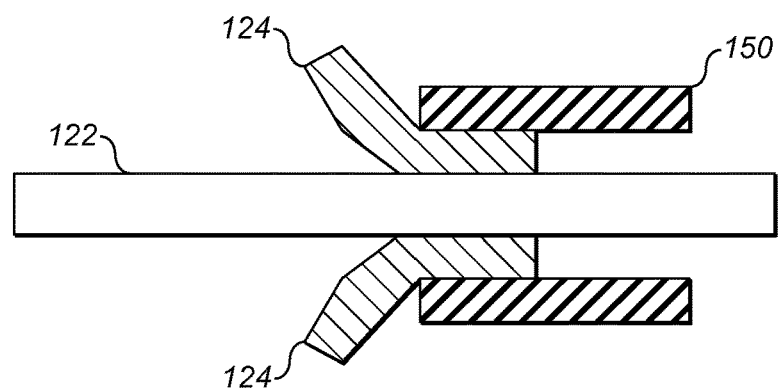
FIG. 16 illustrates schematically an example of fitting mixing elements.

In the arrangement of FIG. 16, individual mixing elements 124 or pairs of mixing elements 124 are attached to the elongate central body 122 by means of a tube, tape or other binding structure 150, for instance heat shrink tubing or adhesive lined shrink fit tubing. This structure could actually be part of the manifold structure.

Figure 17:
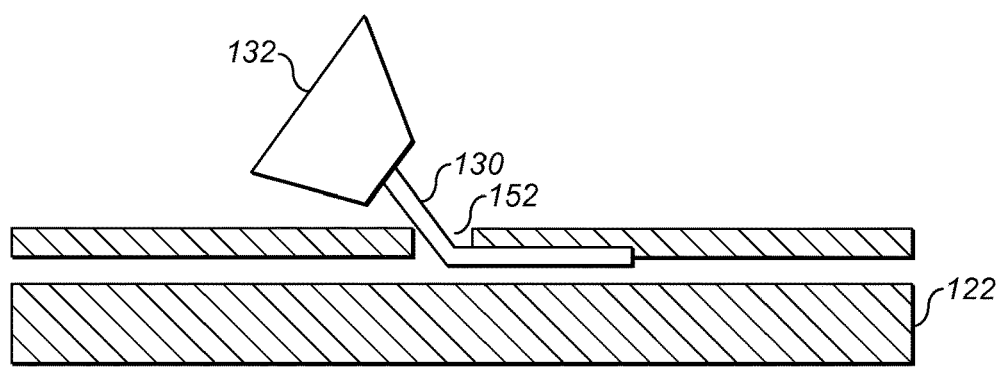
FIG. 17 illustrates schematically an alternative example of fixing a mixing element.

For mixing elements such as described with reference to FIGS. 8 and 9 having masts, roots or the like for instance made from wires comprised of materials with shape memory or super elastic properties (for example metals such as Nitinol or shape memory polymers as provided by companies such as in mNemoscience GmbH), it is possible to provide apertures 152 in the elongate central body 122 into which those roots 130 can be inserted and fixed as illustrated in FIG. 17. Alternatively the mixing elements and their roots could be insert molded into the elongate central body 122. In other words, the elongate central body 122 is formed around the root 130 of the mixing element.

As illustrated in FIG. 7, it is also possible for individual mixing elements to be cut from the wall of the elongate central body and bent out to a desired angle. When manufactured from a shape memory polymer or metal, this could be programmed with the desired stiffness and deployment characteristics.

As discussed above, it is proposed to use a sheath, such as sheath 140 for retaining the mixing elements in their stowed state. However, mixing elements could alternatively be self-actuating using shape memory effects via both shape memory metals and shape memory polymers.

As mentioned above, the described mixers could be used with any appropriate catheter for taking multiple samples. However, a preferred embodiment is constructed using an elongate central body which is formed from multi-lumen tubing. In particular, the elongate central body preferably includes and defines a plurality of elongate passageways or lumens along its length each of which can be connected to a collection port and used to collect a respective sample.

Figure 18:
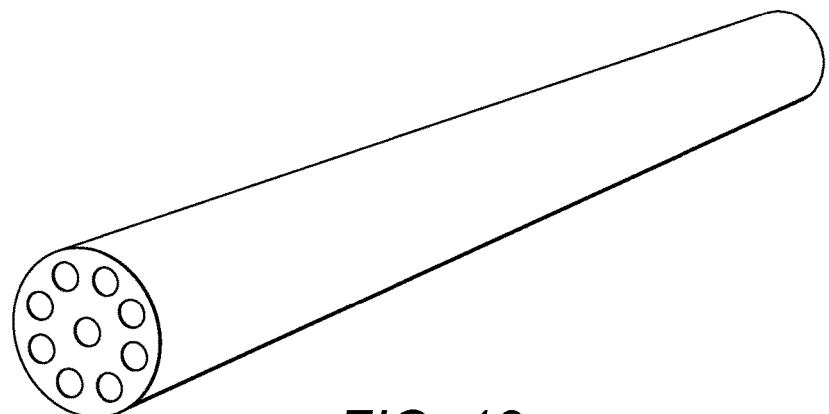
FIG. 18 illustrates schematically a multi-lumen tube.

A variety of different designs of multi-lumen tubing which could be used as part of an elongate central body of the catheter. FIG. 18 illustrates schematically a multi-lumen tube.

FIGS. 19(a) to (e) illustrate a variety of different multi-lumen tube arrangements, suitable for use with over-the-wire (OTW) catheter introduction techniques.

As illustrated, the multi-lumen tubing includes a plurality of lumens 160 arranged circumferentially around the periphery of the elongate central body, each lumen being suitable for connection to a respective connection port and collecting a respective sample. In the illustrated embodiments, a central elongate hole 162 is also provided for receiving a guidewire for the catheter.

As illustrated, a variety of different arrangements are possible. FIGS. 19(a) to (e) illustrate respectively elongate central bodies having ten lumens of 200 μm diameter, 8 lumens of 240 μm diameter, 5 lumens of 400 μm diameter, 8 lumens of 400 μm and 10 lumens of 400 μm diameter. Choice for a preferred embodiment depends on the priority between rate of collection, longitudinal spatial resolution and total cross sectional area of lumen. Priorities would be to minimise the diameter (ideally suitable for use in a 2.00 mm (6F) or smaller guide catheter) then maximise the resolution and accept an extended time to collect sufficient volume. For use in conjunction with a 2.00 mm (6F) guide catheter, the outside diameter of the catheter in the stowed position would be less than 1.5 mm.

Figure 19:
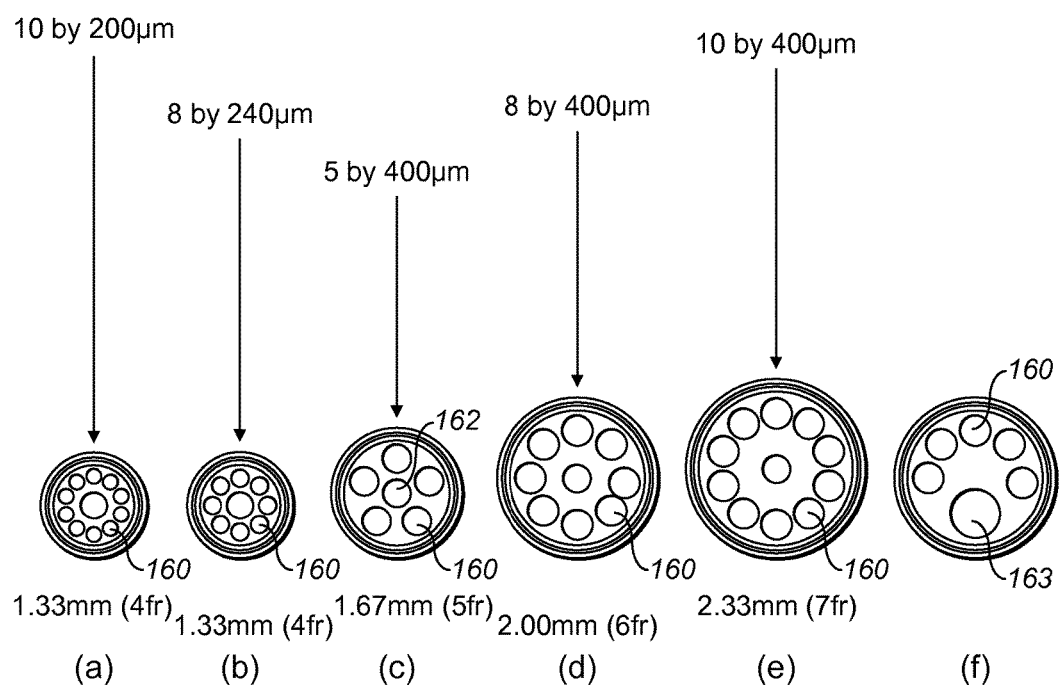
FIGS. 19(a) to (e) illustrate cross-sections of multi-lumen tubing suitable for use in embodiments of the present invention.
FIG. 19(f) illustrates a cross-section of alternative multi-lumen tubing suitable for use in another embodiment of the present invention.

FIG. 19(f) illustrates, schematically, an alternative multi-lumen tube arrangement suitable for use with rapid exchange (Rx) catheter introduction techniques. In this arrangement, the collection lumens 160 are offset with respect to a guidewire lumen 163. With this configuration, the guidewire lumen can have an exit aperture for an associated rapid exchange guidewire whereby the guidewire can exit without crossing any of the collection lumens 160.

Individual lumens 160 may be connected directly to respective collection ports at the outer surface of the elongate central body, for instance as was illustrated schematically in FIG. 1. However, mixers may be used which provide effective radial mixing on only one side of the elongate central body so as to carry biomarkers from the boundary layer of a blood vessel to the elongate central body. With such arrangements, if a connection port happened to be positioned on the opposite side of the elongate central body to the source of biomarkers to be sampled, then reduced sampling efficiency might occur.

Figure 20:
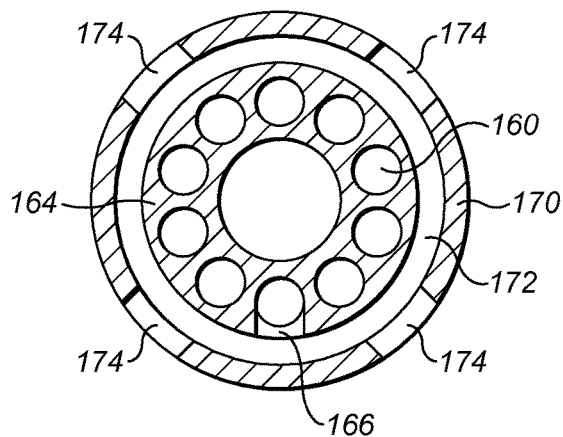
FIG. 20 illustrates schematically a manifold for use in a preferred embodiment of the present invention.

FIG. 20 illustrates one arrangement in which the collection area includes an outer wall 170 surrounding the central elongate body 164 so as to define a circumferential gap or manifold 172 between the outer wall 170 and elongate central body 164. Through holes 174 are provided through the outer wall 170 at positions around the entire circumference of the outer wall 170 such that the manifold 172 communicates with fluid outside the outer wall 170. This is also illustrated in FIG. 6. A collection port 166 is provided in the outer surface of the elongate central body communicating with a respective lumen 160. The collection port 166 is able to collect a sample from fluid in the manifold 172. However, since the manifold 172 communicates with fluid from around the entire periphery of the catheter by means of the through holes 174, the collection port 166 is thus able to collect samples of biomarkers even if these emanate from an opposite side of the catheter.

FIG. 20 illustrates an arrangement where only one collection port 166 is provided for collecting samples in a respective collection area. However, it is also possible for others of the lumens 160 illustrated in FIG. 20 to connect to collection ports in the same collection area. For instance, two diametrically opposed lumens 160 could both connect to respective collection ports in the same collection area.

Figure 21:
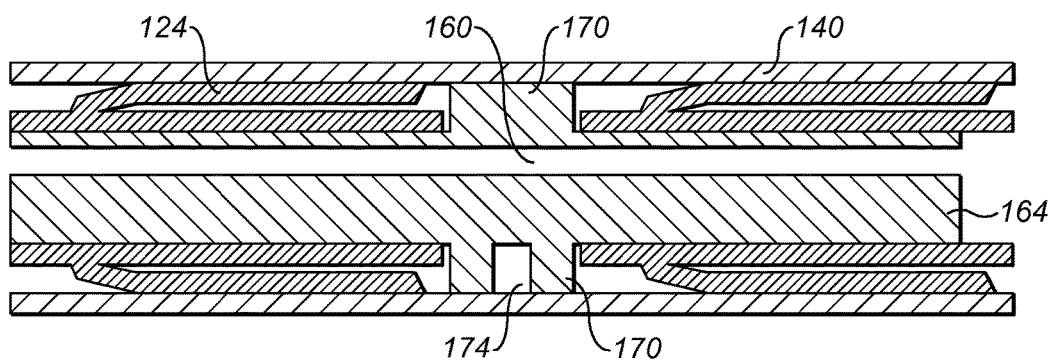
FIG. 21 illustrates schematically a sheath for sealing with a manifold.

FIG. 21 illustrates schematically an arrangement using an outer wall 170 where a single sheath 140 is used to deploy and constrain the mixing elements 124 and can also seal the through holes 174 of a manifold. The sheath 140 holds the mixing elements 124 down and engages the raised outer wall 170.

Figure 22:
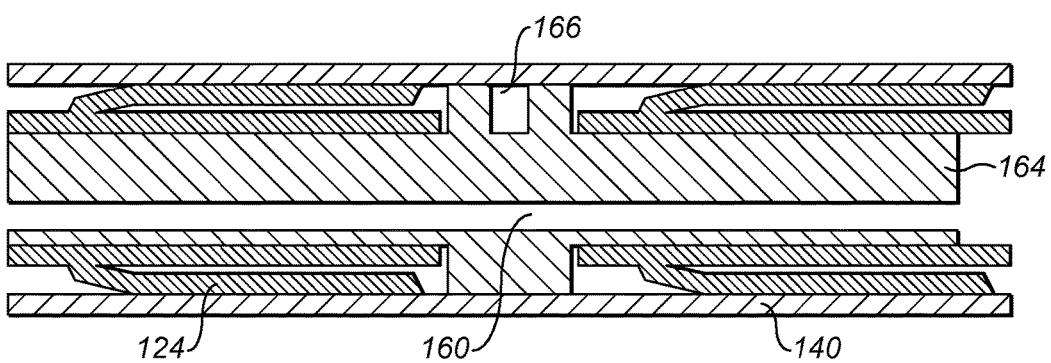
FIG. 22 illustrates schematically a sheath for sealing with a raised portion of the catheter.

FIG. 22 illustrates schematically a similar arrangement without the use of a manifold where the collection port 166 is merely raised and extends to a level to be engaged by the sheath 140.

In some arrangements, it may be desirable for the sheath 140 to seal with the through holes 174 or collection ports 166. However, this is not essential in other arrangements, because the sampling can be controlled by pressure regulation of the lumens.

The lumens and the volume inside the sheath can be saline-filled so as to prevent bubble release when the sheath is retracted and the system deployed. It should be noted that blood pressure is usually sufficient to force blood into exposed lumens and will overcome any inherent air pressure/atmospheric pressure inside the lumens. However, it would be possible to draw samples using negative pressure (relative to air/atmospheric pressure); this can accelerate the rate of flow.

Having obtained samples with the catheter, those samples may be removed for analysis in any convenient manner. It is possible for the samples to be withdrawn from the lumens using suction from either end. In one preferred embodiment, the collection ports 166 or through holes 174 may have a size and shape suitable for receiving a standard laboratory pipette. Where the outer wall 170 is used with a plurality of through holes 174 it may merely be necessary to close all but one of the through holes 174 so as to withdraw a sample from the though hole 174 which remains open.

There now follows a description of how a plurality of samples can be analysed.

After a catheter for obtaining a plurality of samples has been inserted into a blood vessel, such as a coronary artery, it is possible to obtain an image of the position of the catheter in the blood vessel.

The catheter may be inserted into a blood vessel using conventional Percutaneous Coronary Intervention (PCI) techniques. Accordingly, catheters according to this invention may be introduced by means of standard PCI equipment, including introducers, guidewires and guide catheters. Such introduction may be via over-the-wire (OTW) or via rapid exchange (Rx) techniques, the latter of which is preferred.

Sites of interest within a blood vessel under investigation can be identified by a clinician using known techniques. For example, the clinician might inject contrast media in order to image the blood vessel and to determine sites of interest. Alternatively or additionally, standard imaging tools such as IVUS or the InfraRedx plaque locating system could be used. Once the sites of interest have been identified, the catheter for obtaining a plurality of samples can be introduced as described above. In the case of imaging tools that have been introduced into the blood vessel over a guidewire, the catheter can be introduced following the same guidewire, once the imaging tool has been removed.

The catheter may be tracked within the blood vessel using standard fluoroscopic techniques and may be provided with radio-opaque markers allowing the position of the catheter and each collection port to be recorded, for example as an image. The radio-opaque markers may be located at key reference locations such as at the sheath tip and in the blood collection regions. Optionally, a radiopaque marker band may be located adjacent to each blood collection port.

With this data, it becomes possible later to overlay the results of any analysis of the samples onto an image of the blood vessel.

When samples for a coronary artery are to be analysed, it is preferred that the total length of sampling is sufficient to include the majority of the length of the coronary artery and where possible a bulk flow sample from the aortic arch. Hence, it is preferred that the catheter has been inserted previously into a coronary artery and aorta in this way prior to samples being taken.

A plurality of blood samples obtained from a catheter can be tested for multiple proteins. By way of example, proteins can be chosen that are linked in any way to the various stages of cardiovascular disease. Such stages can include healthy endothelium, preliminary endothelium loss of function, early inflammatory, late inflammatory, cap thinning, vulnerable plaque, leakage of thrombotic molecules, plaque rupture, plaque calcification and plaque stabilisation. Examples of possible molecules that are weakly linked with these different stages include ICAM and VCAM-1
Soluble CD40L
any of the matrix metalloprotease family
Soluble E-selectin
Monocyte chemo attractant protein-1
Macrophage colony stimulating factor
P-Selectin
E-Selectin
Cathepsin S
Neutrophil elastase
Endothelial-leukocyte adhesion molecule-1
Intercellular adhesion molecule-1
Soluble Vascular cell adhesion molecule-1
Tissue Factor
Pregnancy associated plasma protein A
Protein-bound-Insulin-like growth factor
Neopterin
Soluble P-Selectin
IL-1, IL-6, IL-7
Choline
Heat Shock Proteins
Chlamydia pneumonia lipopolysaccharides
Degraded interstitial collagen from plaque (Type I+III)
TNF-alpha
Myeloperoxidase The plurality of blood samples obtained from the catheter could also be tasted for mRNA. mRNA is nucleic acid that is used as a temporary instruction to make the protein—it is a biological entity that instructs the formation of a protein from the DNA instruction. It is possible either to look for the gene expression signal that instructs cells to make the protein or to look for the protein itself.

With a catheter removed from its collection site, individual samples can be extracted and retained in individual sample containers corresponding to and with reference to the length over which the samples were collected.

Analysis is possible such that sensitivity will not be compromised by this approach.

In one preferred system, a dilution factor of approximately 12-fold is proposed. Thus, for extracted samples of 2 μl, it is proposed to top up the samples with 23 μl of assay buffer according to appropriate assay protocols.

In one system, it is proposed to use the multiplex Luminex (trade mark) platform for detection purposes. According to this arrangement, multiple different classes of 6 μM beads are incubated with the diluted sample and the proteins of interest are bound by antibodies fixed to the beads. The bound proteins are then detected bead by bead in a specialised flow cytometer. As part of this process, it is possible to use LINCOplex (trade mark) multiplex assays as provided by Linco Research Inc. This allows detection of a plurality of proteins simultaneously at low picogram/ml levels.

Thus, the extracted and diluted samples are analysed to look for protein or nucleic acid or drugs using a highly multiplex assay such that many analytes can be measured within each sample. Systems for protein analysis, such as the Luminex system, will allow analysis of up to 100 proteins at sensitivities of approximately one picogram/ml.

As part of preferred analysis of the extracted samples, the assay data is normalised to a reference analyte, such as a protein, present in each sample. The reference protein is one having a concentration which can be expected to be constant throughout the length of blood vessel in which the catheter had been used. In particular, it is a protein that is not produced or absorbed in this region of the blood vessel. Examples, particularly for coronary arteries, include serum albumin or gamma globulin. This additional "reference" protein assay will be run on each separate sample extracted from the catheter.

Data from any one assay can be used to determine the mass of a particular protein in that corresponding sample by comparing the sample's data point against a predetermined reference curve. Because the concentration of the reference protein can be assumed to be constant in each sample, then the determined mass will be directly proportional to the amount of sample volume assayed.

In this way, the data obtained for each biomarker for all of the samples extracted from the catheter can be normalised by reference to the reference protein.

In one system, a volume correction value is determined by calculating an average of all of the reference values from all of the extracted samples. The individual biomarker data can then be normalised with reference to this volume correction value. Optionally, each sample's reference value is expressed as a fraction of the average reference value.

The volume correction value can then be used to adjust the data of all proteins in all samples so that it is possible to correct for variations in volume transferred from the catheter. In particular, this is achieved by multiplying each raw data value by the correction factor.

The following table illustrates data for a series of eight samples (A to H) for analysis.

biomarker 2. Other values of reference protein are obtained for other samples. For example, sample E has a value of 19 for the reference protein. Using this value for the reference protein, it would be possible to normalise the sample E raw data of 185 for biomarker 1 and 4,250 for biomarker 2 with regard to sample A. In particular, for sample E, the biomarker raw data could be multiplied by 17/19.

As illustrated, in this arrangement, an average reference amount is obtained for all of the samples by averaging the individual reference values for the reference protein across all of the samples. By comparing the actual individual reference values for respective samples with the average reference amount, individual correction factors are obtained for each sample. The correction factors can then be applied to the raw biomarker data so as to normalise that data across all of the samples.

The corrected values for the biomarkers/molecules can be presented by any user interface, either numerically or graphically. A user can then make use of this data as required. In particular, molecular concentrations could be compared with the most upstream sample port and expressed as a relative difference.

In a case where a catheter has been inserted in a coronary artery, preferably the most upstream collection port samples from the aortic arch. It is then possible to show a differential of blood within the coronary artery relative to blood incoming to the coronary artery. Samples taken from parts of the catheter which were adjacent to respective parts of the coronary artery show an increase in specific molecules and thus the release of these molecules within those areas of the coronary artery as compared with levels in general circulation.

The catheter may be provided with radio-opaque markers to facilitate correlation of regions of biomarker heterogeneity with the location of the catheter within the blood vessel at time of capture. This enables localised regions of biological or chemical heterogeneity in a blood vessel to be identified.

| | Blood extracted and assayed in e.g. a microtitre plate well | | | | | | | |
|---|---|---|---|---|---|---|---|---|
| | A | B | C | D | E | F | G | H |
| Reference protein amount from assay | 17 | 15 | 16 | 17 | 19 | 21 | 16 | 17 |
| Average ref amount across all assays | 17.25 | 17.25 | 17.25 | 17.25 | 17.25 | 17.25 | 17.25 | 17.25 |
| Correction factor | 1.01 | 1.15 | 1.08 | 1.01 | 0.91 | 0.82 | 1.08 | 1.01 |
| Raw data for Biomarker 1 cone from assay | 140 | 159 | 179 | 190 | 185 | 182 | 170 | 160 |
| Corrected concentration of Biomarker 1 | 142 | 183 | 193 | 193 | 168 | 150 | 183 | 162 |
| Raw data for Biomarker 2 cone from assay | 4000 | 3790 | 3800 | 3960 | 4250 | 4700 | 3900 | 3870 |
| Corrected concentration of Biomarker 2 | 4059 | 4359 | 4097 | 4018 | 3859 | 3861 | 4205 | 3927 |

As illustrated, raw data is available for a reference protein and also for biomarkers 1 and 2. Thus, for sample A, a value of 17 is obtained for the reference protein, a value of 140 is obtained for biomarker 1 and a value of 4,000 is obtained for In one arrangement, the various information contained for the biomarkers can be displayed directly in relation to positions along the blood vessel, for instance the coronary artery.

As mentioned above, a catheter can be provided with radio-opaque markers. With an image of the blood vessel, such as the coronary artery, available, the particular biomarker values can be overlayed onto that image, either numerically or graphically. It is possible to provide an apparatus and a display for processing data appropriately and presenting the data in this way. Appropriate computer programs/software may also be provided which can be loaded and run to achieve this effect.

Figure 23:
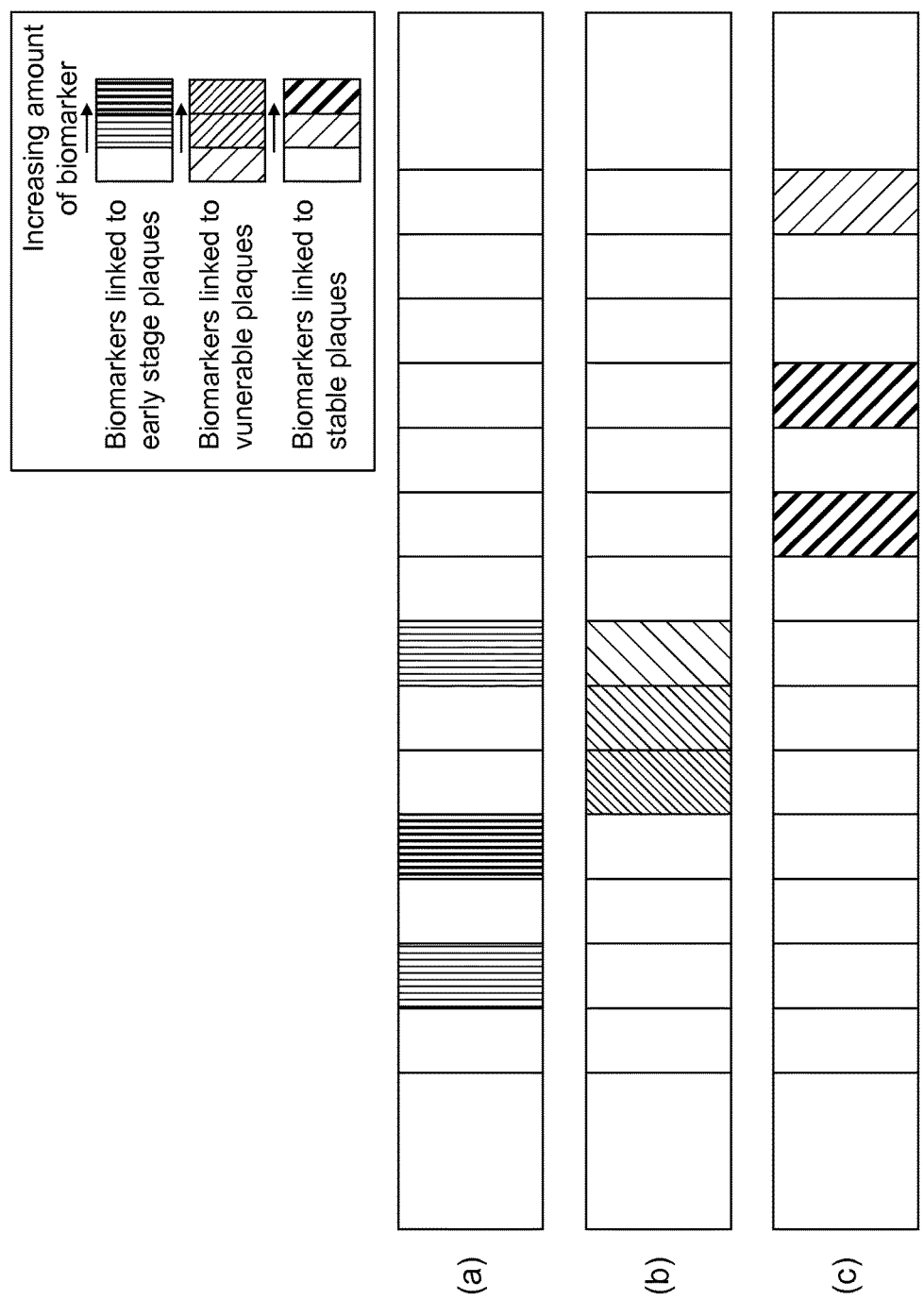
FIGS. 23(a) to (c) illustrate respectively for the same length of blood vessel three different individual/groups or other combinations of molecules or biomarkers associated with different stages in plaque evolution.

FIG. 23 illustrates schematically an example of displaying data relative to an image of a blood vessel, such as a coronary artery.

FIGS. 23(a), (b) and (c) illustrate respectively for the same length of blood vessel three different individual/groups or other combinations of molecules or biomarkers associated with different stages in plaque evolution. The stages of the various plaques found as a result of the detected release are shown at positions relative to the length of the blood vessel.

A blood vessel is shown schematically in transfer section with a series of boxes overlayed onto it, each box representing a sampling location.

The different molecules can be analysed and linked to stages in plaque development so as to create a risk assessment profile. In the illustrated example, early stage, vulnerable and stable plaques are shown. Those different stages can be illustrated in different respective forms, for instance with different respective intensities or colours. The intensity or colour in each example can then show the amount of release and hence the scale threat of any plaque.

It is proposed that this technique could be used to determine the effectiveness of clinical therapy. In particular, the number and extent of truly vulnerable plaques could be assessed over time.

The approach could also be used to develop proprietary biomarkers. The approach allows the collection and interpretation of accurate molecular information. Molecular data may be obtained and analysed at multiple points throughout a patient's therapy (and indeed with multiple patients). In this way, it becomes possible to make a correlation between molecular expression and clinical outcome. By using this information, it becomes possible to identify molecules having biomarker predictive status.

The analysis can also be used to provide information regarding the impact of local device-based therapy, such as stenting or angioplasty. In particular, it is possible to assay and analyse molecules associated with damage, such as inflammatory processes or the release of endothelial wall material. It is then possible to provide accurate assessment of the extent and location of damage and, if used again, its recovery.

Figure 24A:
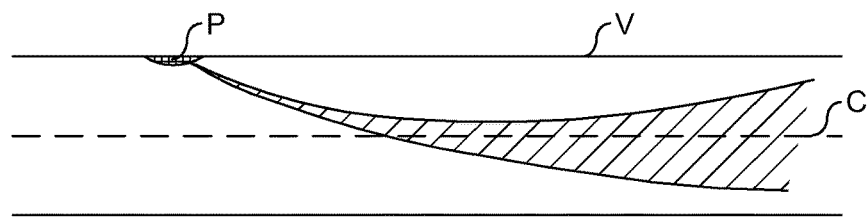
FIGS. 24(a) and (b) illustrate the concentration of biomarker present at the central region of a blood vessel as a result of plaque, where little or no mixing occurs within the blood vessel.

FIGS. 24(a) and (b) and 25(a) and (b) illustrate respectively the concentration of biomarker present at the central region C of a blood vessel V as a result of plaque P.

Figure 24B:
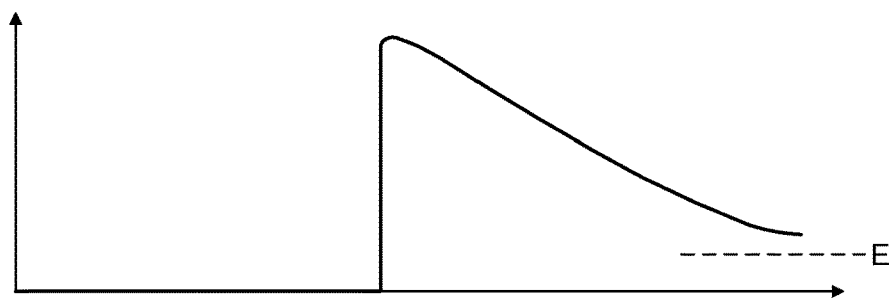

FIG. 24 illustrates the case where little or no mixing occurs within the blood vessel V. As illustrated in FIG. 24(a), the concentration of biomarker takes the form of a plume drifting and then gradually spreading within the flow of blood in the blood vessel V. As illustrated in FIG. 24(b), when the plume reaches the centre C of the blood vessel V, the detected concentration of biomarker rises very rapidly to a relatively high concentration. However, the detected concentration then almost immediately starts to drop. Indeed, as the plume spreads out along the blood vessel, the detected concentration will gradually drop to the concentration where the biomarker is spread evenly throughout the cross-section of the blood vessel as indicated by the dashed line E.

Figure 25A:
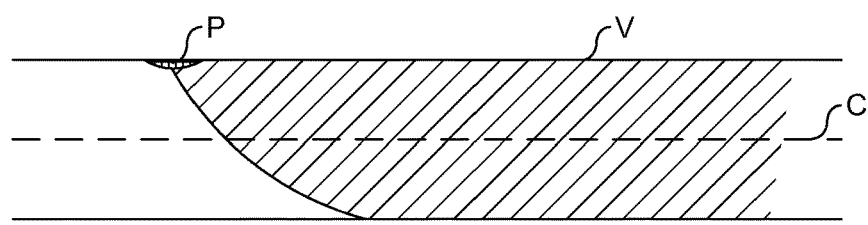
FIGS. 25(a) and (b) illustrate the concentration of biomarker present at the central region of a blood vessel as a result of plaque, where mixing within the blood vessel is used.
Figure 25B:
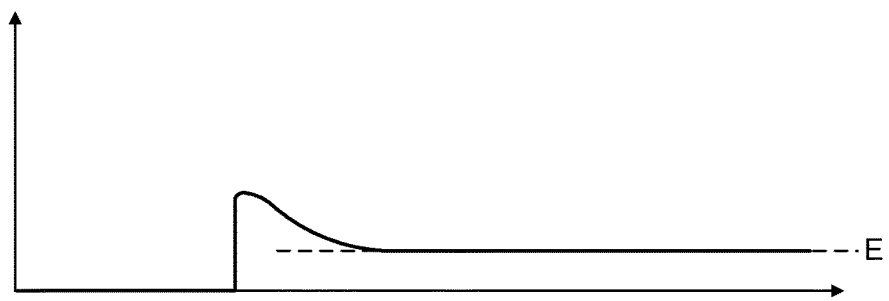

FIG. 25(a) illustrates somewhat schematically how a biomarker is distributed in the flow of blood in the blood vessel V when mixing is used. In particular, depending upon the efficiency of the mixing, the biomarker will very rapidly spread across the entire cross section of the blood vessel and reach the even distribution indicated in FIG. 25(b) with dashed line E. When the biomarker distribution first reaches the central region C, it will already have been mixed significantly and, hence, will not be at the high concentrations discussed above for FIG. 24. In fact, it is likely only slightly to exceed the even distribution E before rapidly lowering to that even distribution.

In either the unmixed or mixed example, it will be seen that the first detected position of the biomarker is always downstream of the actual plaque P. For the unmixed example of FIG. 24, the length of offset is considerably greater and also the predictability of that offset is lower.

For either case, it is proposed to introduce an additional step between obtaining the corrected concentration data for the biomarkers and displaying that information, for instance as illustrated in FIG. 23. In particular, it is proposed to introduce an additional correction with regard to offset. Taking into account factors such as blood vessel diameter, flow rates and catheter properties, it becomes possible to offset the displayed concentrations such that they are located relative to the image of the blood vessel in positions more representative of the actual positions of any plaque, etc.

Because, as mentioned above, the offset for a mixed flow is much shorter and more predictable, the mixed flow has significant advantages. When correcting the offset for mixed flow, the characteristics of the mixing can be taken into account. In particular, the accuracy of localisation of biomarker release relative to the position in the artery can be increased by using knowledge of the way by which the mixers intercept and divert flow from the boundary layers of the blood vessel to collection ports along the elongate central body of the catheter.

So far, consideration has been given only to actually detected (and corrected) values. However, when samples are to be analysed that were taken from a catheter using mixing, those actual values are generally smaller and provide more of a step change than a peak for identification by the user.

In view of this, it is also proposed to take a differential of the corrected concentration values for the biomarkers.

Where mixing is employed, the mixed concentration of biomarker is reached very rapidly. In comparison, where mixing is not used, the concentration is somewhat variable. By taking a differential of the values, a very clear indication of initial detection of a biomarker can be obtained. Resulting differential values can be displayed as illustrated in FIG. 23 and, additionally, can be corrected for offset in the manner discussed above.

The invention claimed is:

1. A vascular catheter for taking a plurality of discrete blood samples in vivo from within a length of a blood vessel, the vascular catheter including:
    an elongate central body arranged to be inserted, over a guidewire, into the blood vessel; a plurality of longitudinally spaced blood collection areas defined along the elongate central body, the plurality of collection areas configured for collecting the discrete blood samples from the lumen of the blood vessel, each of the blood collection areas having at least one blood collection port; and
    at least one static mixer comprising a respective plurality of mixing elements extending radially outwardly of the elongate central body and arranged at successive positions along and at corresponding successive angles around the elongate central body, the at least one static mixer being in non-contiguous contact with the blood vessel wall so as to maintain at least one open region between the plurality of mixing elements of the at least one static mixer and the blood vessel wall for blood flow, the at least one static mixer arranged to create a flow of blood from a boundary layer at a wall of the blood vessel, around the entire periphery of the blood vessel, to the elongate central body so as to enable the plurality of longitudinally spaced blood collection areas to collect the discrete blood samples from the boundary layer.

2. The vascular catheter according to claim 1 wherein the at least one static mixer is deployable from an inactive state for insertion into a blood vessel to an active state so as to interfere with a boundary layer of the blood vessel, wherein in the inactive state the at least one static mixer is closer to the elongate central body than when in the active state.

3. The vascular catheter according to claim 1 wherein each of the plurality of mixing elements is pivotally attached to the elongate central body so as to pivot in the elongate direction of the elongate central body and towards and away from the elongate central body.

4. The vascular catheter according to claim 1 wherein each of the plurality of mixing elements has the form of a paddle extending in radial and tangential directions with respect to the elongate central body.

5. The vascular catheter according to claim 1 wherein each of the plurality of mixing elements has a planar extent following a respective plane through a respective diameter of the elongate central body.

6. The vascular catheter according to claim 1 wherein the relative angle around the elongate central body between mixing elements at adjacent positions along the elongate central body is 90°.

7. The vascular catheter according to claim 1 wherein the plurality of mixing elements are arranged in pairs, each pair of mixing elements being positioned at a respective position along the elongate central body and individual mixing elements of a pair of mixing elements being on opposite respective sides of the elongate central body.

8. The vascular catheter according to claim 7 wherein the at least one static mixer includes at least two pairs of mixing elements.

9. The vascular catheter according to claim 1 wherein the plurality of mixing elements are spaced and shaped such that when mixing elements at adjacent positions along the elongate central body are deflected so as to be parallel with an outer surface of the elongate central body, the mixing elements at adjacent positions do not overlap.

10. The vascular catheter according to claim 1 wherein each of the blood collection areas includes at least one blood collection port located at a respective position along the elongate central body for collecting a respective discrete blood sample at that position.

11. The vascular catheter according to claim 10 wherein the elongate central body includes at least one lumen extending internally along the elongate central body connecting with the at least one blood collection port in each of the blood collection areas.

12. The vascular catheter according to claim 11 wherein the elongate central body includes a plurality of lumens extending internally along the elongate central body, each of the plurality of lumens connecting with a respective blood collection port.

13. The vascular catheter according to claim 10 wherein at each of the plurality of blood collection areas, the elongate central body includes an outer wall having an outwardly facing surface and an inwardly facing surface and an inner body in which the at least one blood collection port is defined, the inwardly facing surface of the outer wall and the inner body defining a circumferential gap therebetween and a circumferential array of through holes being defined through the outer wall between the inwardly facing surface and the outwardly facing surface such that the circumferential gap forms a manifold feeding the at least one blood collection port from a plurality of radial directions.

14. The vascular catheter according to claim 1 including a plurality of static mixers arranged along the length of the central body wherein each of the plurality of collection areas is defined between adjacent ones of said static mixers.

15. The vascular catheter according to claim 14 wherein at least one collection area is defined between adjacent static mixers.

16. The vascular catheter according to claim 14 where a collection area is defined at one end of the catheter so as to be upstream of any mixer when in use.

17. The vascular catheter according to claim 1 further comprising a sleeve within which the elongate central body and the at least one mixer can be stowed, the sleeve being withdrawable so as to expose the at least one mixer and the at least one collection area.

18. The vascular catheter of claim 1, the plurality of mixing elements configured to mix blood as it flows through the at least one static mixer along the elongate central body thereby to create a flow of blood from a boundary layer at a wall of the blood vessel, around the entire periphery of the blood vessel, to the elongate central body so as to enable the blood collection area to collect the plurality of discrete blood samples from the boundary layer, wherein at least one of the plurality of mixing elements, when in a deployed, active state, extends away from the elongate central body at least partially in a respective direction which is angularly offset with respect to a plane perpendicular to a longitudinal axis of the elongate central body.

19. The vascular catheter of claim 18 wherein the relative angle around the elongate central body between mixing elements at adjacent positions along the elongate central body is 90°.

20. The vascular catheter of claim 18 wherein the plurality of mixing elements are arranged in pairs, each pair of mixing elements being positioned at a respective position along the elongate central body and individual mixing elements of a pair of mixing elements being on opposite respective sides of the elongate central body.

21. The vascular catheter of claim 20 wherein an open region defined by one of the pairs of mixing elements is obstructed by an adjacent pair of mixing elements.

22. The vascular catheter of claim 18 wherein at least one of the plurality of longitudinally spaced blood collection areas is defined at one end of the vascular catheter so as to be upstream of any mixer when in use.

23. The vascular catheter of claim 1, the at least one static mixer configured to sequentially separate, rotate and recombine a flow of blood as it moves through the mixer along the elongate central body so as to effect mixing of blood across the radius of the blood vessel.

24. The vascular catheter of claim 23 wherein the relative angle around the elongate central body between mixing elements at adjacent positions along the elongate central body is 90°.

25. The vascular catheter of claim 23 wherein the plurality of mixing elements are arranged in pairs, each pair of mixing elements being positioned at a respective position along the elongate central body and individual mixing elements of a pair of mixing elements being on opposite respective sides of the elongate central body.

26. The vascular catheter of claim 25 wherein an open region defined by one of the pairs of mixing elements is obstructed by an adjacent pair of mixing elements.

27. The vascular catheter of claim 23 wherein at least one of the plurality of longitudinally spaced blood collection areas is defined at one end of the vascular catheter so as to be upstream of any mixer when in use.

28. The vascular catheter of claim 1 wherein the at least one static mixer, when in a deployed, active state, extends away from the elongate central body at least partially in a direction which is angularly offset with respect to a plane perpendicular to a longitudinal axis of the elongate central body.

29. The vascular catheter of claim 1 wherein the plurality of mixing elements are configured to mix blood as it flows through the mixer along the elongate central body thereby to create a flow of blood from a boundary layer at a wall of the blood vessel, around the entire periphery of the blood vessel, to the elongate central body so as to enable the blood collection area to collect blood samples from the boundary layer,
wherein at least one of the plurality of mixing elements, when in a deployed, active state, extends away from the elongate central body at least partially in a respective direction which is angularly offset with respect to a plane perpendicular to a longitudinal axis of the elongate central body.

30. The vascular catheter of claim 1 wherein at least one of the plurality of mixing elements, when in a deployed, active state, extending away from the elongate central body at least partially in a respective direction which is angularly offset with respect to a plane perpendicular to the longitudinal axis of the elongate central body, the at least one static mixer configured to sequentially separate, rotate and recombine a flow of blood as it moves through the at least one static mixer along the elongate central body so as to effect mixing of blood across the radius of the blood vessel.

31. A vascular catheter for sampling blood in vivo from a blood vessel, comprising:
 a flexible catheter body for insertion over a guidewire into the blood vessel;
 a plurality of longitudinally spaced blood collection ports for simultaneously capturing discrete blood samples taken along a length of the blood vessel; and
 a static mixer located upstream of the plurality of longitudinally spaced blood collection ports and adapted to be deployed radially outwardly along a section of the catheter body for continuously mixing blood substantially across the entire radial extent of the blood vessel to include, in the discrete blood samples, blood present in a boundary layer at the blood vessel wall as blood flows through the static mixer,
 in which the deployable static mixer comprises a plurality of groups of mixing elements, each group of mixing elements being arranged at a respective position along the section of the catheter body and angularly offset relative to any preceding group of mixing elements, thereby in use to sequentially separate, rotate and recombine blood as it flows through the static mixer.

32. A vascular catheter according to claim 1, wherein the plurality of mixing elements deploy by expanding outwardly from the elongate central body.

* * * * *